(12) United States Patent
Pinter

(10) Patent No.: US 6,815,201 B2
(45) Date of Patent: Nov. 9, 2004

(54) HIV-1 GP120 V1/V2 DOMAIN EPITOPES CAPABLE OF GENERATING NEUTRALIZING ANTIBODIES

(75) Inventor: Abraham Pinter, Brooklyn, NY (US)

(73) Assignee: The Public Health Research Institute of the City of New York, Inc., Newark, NJ (US)

( * ) Notice: Subject to any disclaimer, the term of this patent is extended or adjusted under 35 U.S.C. 154(b) by 0 days.

(21) Appl. No.: 10/038,407

(22) Filed: Jan. 2, 2002

(65) Prior Publication Data

US 2003/0105282 A1 Jun. 5, 2003

Related U.S. Application Data

(63) Continuation of application No. 09/508,208, filed as application No. PCT/US98/18679 on Sep. 8, 1998, now abandoned.
(60) Provisional application No. 60/058,155, filed on Sep. 8, 1997.

(51) Int. Cl.[7] .................... C12N 5/16; C12Q 1/70; C12P 21/06; C12P 21/08
(52) U.S. Cl. .................... 435/339.1; 435/5; 435/6; 435/69.7; 530/387.3; 530/388.35

(58) Field of Search .................... 435/5, 6, 69.7, 435/339.1; 530/387.3, 388.35

(56) References Cited

U.S. PATENT DOCUMENTS 5,336,603 A     8/1994   Capon et al. .............. 435/69.7
5,643,756 A   *   7/1997   Kayman et al. ........... 435/69.7

OTHER PUBLICATIONS

Ashkenazi et al., "Resistance of primary isolates of human immunodeficiency virus type 1 to soluble CD4 . . . " Proc. Nat'l. Acad. Sci. USA 88:7056–7060, 1991.

Bebbington et al., "High–level expression of a recombinant antibody from myeloma cells using a glutabmine . . . " Bio/Technology 10:169–175, 1992.

(List continued on next page.)

Primary Examiner—Hankyel T. Park
(74) Attorney, Agent, or Firm—Fish & Richardson P.C.

(57) ABSTRACT

The invention features a protein which includes a gp120 V1/V2 domain of an HIV-1 strain and not a gp120 V3 domain of an HIV-1 strain, which protein does not substantially bind CD4. The gp120 V1/V2 domain of the protein displays an epitope which is recognized by an antibody which neutralizes at least one HIV-1 primary isolate with a $ND_{90}$ of less than 100 μg/ml.

32 Claims, 13 Drawing Sheets

```
- - - S - - - G - - - - - - - F - - - - - I - - - -   HXB2
- - - - - - - - - - - - - - - - - - - - - I - - - -   Case-A2

S F N I T T S I R D K V Q K E Y A L F Y K L D V V P I D    Most common clade
55 55 46 42 46 54 43 45 47 31 52 32 45 50 45 47 55 40 51 47 42 52 55 33 47 54 52 44  /55

* * Y V S   N R G N R M K R Q N * F L N R Y * I I S V E   2nd most common
  4 11 8   1 7 5 5 18 2 13 6 2 3 4  10 4 4 7 1   21 3 1 1 5   /55
|                                                                              |
185                                                                          185
```

OTHER PUBLICATIONS

Bou–Habib et al., "Cryptic nature of envelope V3 region epitopes protects primary monocytotropic human immunodeficiency . . . " J. of Virol. 68(9):6006–6013, 1994.

Burton et al., "Efficient neutralization of primary isolates of HIV–1 by a recombinant human monoclonal antibody" Science 266:1024–1027, 1994.

Chamat et al., "Two major groups of neutralizing anti–gp120 antibodies exist in HIV–infected individuals" J. of Immun. 149(2):649–654, 1992.

Conley et al., "Neutralization of primary human immunodeficiency virus type 1 isolates by the broadly anti– V3 . . . " J. of Virol. 68(11):6994–7000, 1994.

Conley et al., "Neutralization of divergent human immunodeficiency virus type 1 variants and primary isolates . . . " Proc. Nat'l. Acad. Sci. USA 91:3348–3352, 1994.

Cordell et al., "Rat monoclonal antibodies to nonoverlapping epitopes of human immunodeficiency virus type 1 . . . " Virology 185:72–79, 1991.

D'Souza et al., "Neutralization of primary HIV–1 isolates by anti–envelope monoclonal antibodies" AIDS 9(8):867–874, 1995.

D'Souza et al., "Evaluation of monoclonal antibodies to HIV–1 envelope by netralization and binding assays: . . . " AIDS 8(2):169–181, 1994.

Fouts et al., "Neutralization of the human immunodeficiency virus type 1 primary isolate JR–FL by human monoclonal . . . " J. of Virol. 71(4):2779–2785, 1997.

Fishwald et al., "High–avidity human IgGk monoclonal antibodies from a novel strain of minilocus transgenic mice" Nature Biotechnology 14:845–851, 1996.

Fung et al., "Identification and characterization of a neutralization site within the second variable region of human . . . " J. of Virology 66(2):848–856, 1992.

Gao et al., "Genetic variation of HIV type 1 in four world health organization–sponsored vaccine evaluation sites: . . . " AIDS Research and Human Retroviruses 10(11):1359–1368, 1994.

Golding et al., "Neutralization of HIV–1" AIDS Res. And Human Retroviruses 10(6):633–643, 1994.

Gomatos et al., "Relative inefficiency of soluble recombinant CD4 for inhibition of infection by monocyte–tropic . . . " J. of Immunol. 144(11):4183–4188, 1990.

Guo et al., "HIV acquires functional adhesion receptors from host cells" AIDS Res. And Human Retroviruses 11(9):1007–1013, 1995.

Hanson, C., "Measuring vaccine–induced HIV neutralization: Report of a workshop" AIDS Res. And Human Retroviruses 10(6):645–648, 1994.

Hildreth et al., "Involvement of a leukocyte adhesion recepotr (LFA–1) in HIV–induced syncytium formation" Science 244:1017–1116, 1989.

Ho et al., "Another discontinues epitope on glycoprotein gp120 that is important in human immunodeficiency . . . " Proc. Nat'l. Acad. Sci. USA 88:8949–8952, 1991.

Ho et al., "Conformational epitope on gp120 important in CD4 binding and human immunodeficiency . . . " J. of Virol. 65(1):489–493, 1991.

Kayman et al., "Presentation of native epitopes in the V1/V2 and V3 regions of human immunodeficiency . . . " J. of Virol. 68(1):400–410, 1994.

Lee et al., "Enhancement of human immunodeficiency virus type 1 envelope–mediated fusion by a CD4–gp120 complex . . . " J. of Virol. 71(8):6037–6043, 1997.

Mascola, J., "Neutralizing antibody activity in sera from human immunodeficiency virus type 1 vaccine recipients . . . " AIDS Res. And Human Retroviruses 10(2):S55, 1994.

Matthews, T., "Dilemma of neutralization resistance of HIV–1 field isolates and vaccine development" AIDS Res. And Human Retroviruses 10(6):631–632, 1994.

McKeating et al., "Characterization of neutralizing monoclonal antibodies to linear and conformation–dependent . . . " J. of Virol. 67(8):4932–4944, 1993.

Mendez et al., "Functional transplant of megabase human immunoglobulin loci recapitulates human antibody response in mice" Nature Genetics 15:146–156, 1997.

Moore et al., "Primary isolates of human immunodeficiency virus type 1 are relatively resistanct to neutralization . . . " J. of Virol. 69(1):101–109, 1995.

Moore et al., "Antibodies to discontinuous or conformationally sensitive epitopes on the gp120 glycoprotein of . . . " J. of Virol. 67(2):863–875, 1993.

Moore et al., "Probing the structure of the V2 domain of human immunodeficiency virus type 1 surface glycoprotein gp120 . . . " J. of Virol. 67(10):6136–6151, 1993.

Muster et al., "Cross–neutralizing activity against divergent human immunodeficiency virus type 1 isolates induced . . . " J. of Virol. 68(6):4031–4034, 1994.

Olshevsky et al., "Identification of individual human immunodeficiency virus type 1 gp120 amino acids important for CD4 receptor binding" J. of Virol. 64(12):5701–5707, 1990.

Pincus et al., "Temporal analysis of the antibody response to HIV envelope protein in HIV–infected laboratory workers" J. of Clin. Invest. 93:2505–2513, 1994.

Sawyer et al., "Neutralization sensitivity of human immunodeficiency virus type 1 is determined in part by the cell . . . " J. of Virol. 68(3):1342–1349, 1994.

Schutten et al., "Enhancement of infectivity of a non–syncytium inducing HIV–1 by sCD4 and by human antibodies . . . " Scand. J. Immunol. 41:18–22, 1995.

Stamatatos et al., "Binding of antibodies to virion–associated gp120 molecules of primary–like human immunodeficiency . . . " Virology 229:360–369, 1997.

Sullivan et al., "Effect of animo acid changes in the V1/V2 region of the human immunodeficiency virus type 1 gp120 . . . " J. of Virol. 67(6):3674–3679, 1993.

Thali et al., "Discontinuous, conserved neutralization epitopes overlapping the CD4–binding region of human immunodeficiency . . . " J. of Virol. 66(9):5635–5641, 1992.

Tilley et al., "Human and chimpanzee monoclonal antibodies with antiviral activity against HIV–1" AIDS Research Review 3:255–287, 1993.

Trkola et al., "Cross–clade neutralization of primary isolates of human immunodeficiency virus type 1 by human monoclonal . . . " J. of Virol. 69(11):6609–6617, 1995.

Trkola et al., "Human monoclonal antibody 2G12 defines a distinctive neutralization epitope on the gp120 glycoprotein of . . . " J. of Virol. 70(2):1100–1108, 1996.

VanCott et al., "Lack of induction of antibodies specific for conserved, discontinuous epitopes of HIV–1 envelope glycoprotein . . . " J. of Immunol. 155(8):4100–4110, 1995.

Vancott et al., "Differential role of V3–Specific antibodies in neutralization assays involving primary and laboratory–adapted . . . " AIDS Res. And Human Retroviruses 11(11):1379–1391, 1995.

Vijh–Warrier, et al., "Synergistic neutralization of human immunodeficiency virus type 1 by a chimpanzee monoclonal antibody . . . " J. of Virol. 70(7):4466–4473, 1996.

Wang et al., "Sequence diversity of V1 and V2 domains of gp120 from human immunodeficiency virus type 1: . . . " J. of Virol. 69(4):2708–2715, 1995.

Warrier et al., "A novel, glycan–dependent epitope in the V2 domain of human immunodeficiency virus 1 gp120 . . . " J. of Virol. 68(7):4636–4642, 1994.

Westervelt et al., "Macrophage tropism determinants of human immunodeficiency virus type 1 in vivo" J. of Virol. 66(4):2577–2582, 1992.

Wu et al., "Characterization of neutralization epitopes in the V2 region of human immunodeficiency virus type 1 gp120: . . . " J. of Virol. 69(4):2271–2278, 1995.

* cited by examiner

FIG. 1

| Position | HXB2 | Case-A2 | Most common clade /55 | 2nd most common /55 |
|---|---|---|---|---|
| 1 | — | — | S 55 | F 55 |
| 2 | — | — | F 55 (underlined) | * |
| 3 | — | — | N 46 | Y 4 |
| 4 | S | — | I 42 | V 11 |
| 5 | — | — | T 54 | S 8 |
| 6 | — | — | T 46 | — |
| 7 | — | — | S 43 | N 7 |
| 8 | — | — | I 45 | R 5 |
| 9 | — | — | R 47 | G 5 |
| 10 | — | G | D 31 | N 18 |
| 11 | — | — | K 52 | R 2 |
| 12 | — | — | V 32 | M 13 |
| 13 | — | — | Q 45 | K 6 |
| 14 | — | — | K 50 | R 2 |
| 15 | — | — | E 45 | Q 3 |
| 16 | — | — | Y 47 | N 3 |
| 17 | — | — | A 55 (underlined) | * |
| 18 | F | — | L 40 | F 10 |
| 19 | — | — | F 51 | L 4 (underlined) |
| 20 | — | — | Y 47 | N 4 |
| 21 | — | — | K 42 | R 7 |
| 22 | — | — | L 52 | Y 1 |
| 23 | — | — | D 55 (underlined) | * 21 |
| 24 | I | I | V 33 | I 3 |
| 25 | — | — | V 47 | I 3 |
| 26 | — | — | P 54 | S 1 |
| 27 | — | — | I 52 | V 1 |
| 28 | — | — | D 44 | E 5 |

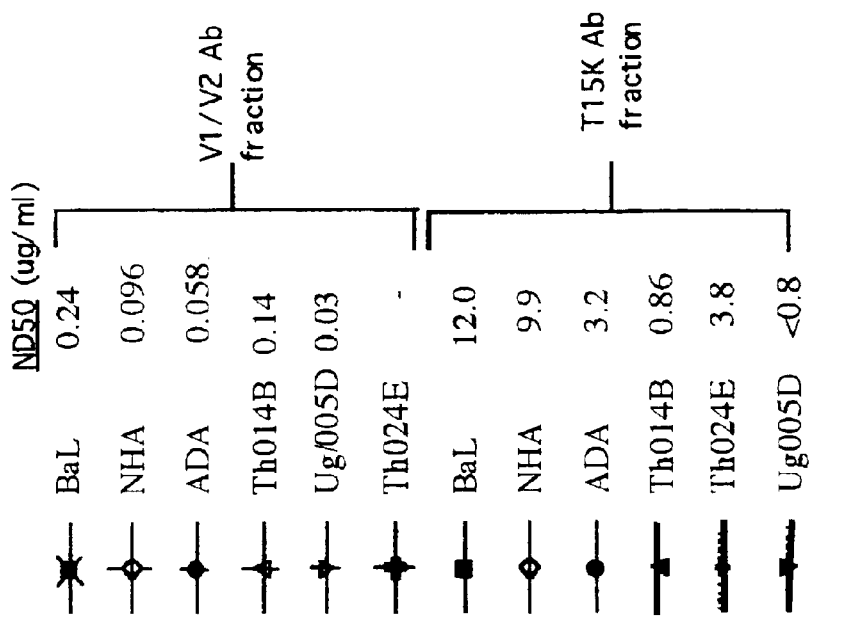
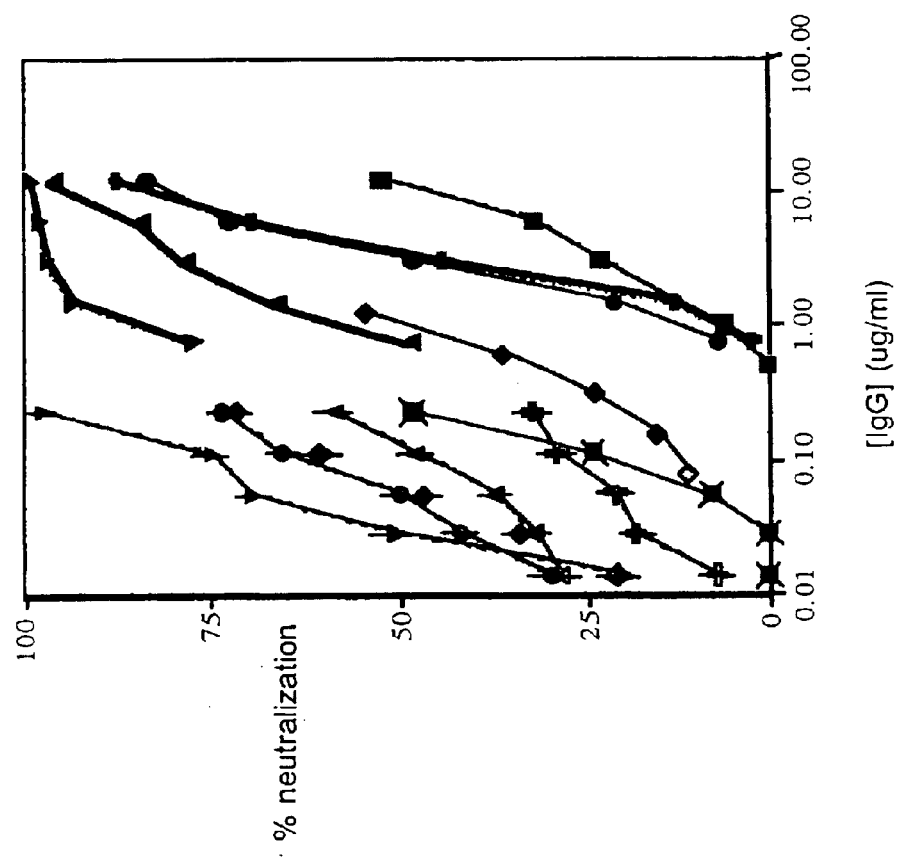
FIG. 4B
FIG. 4A

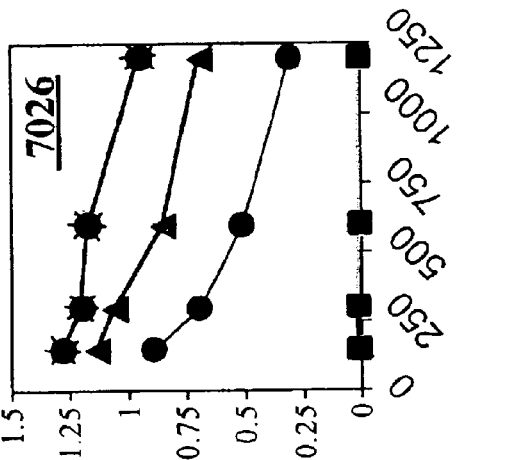
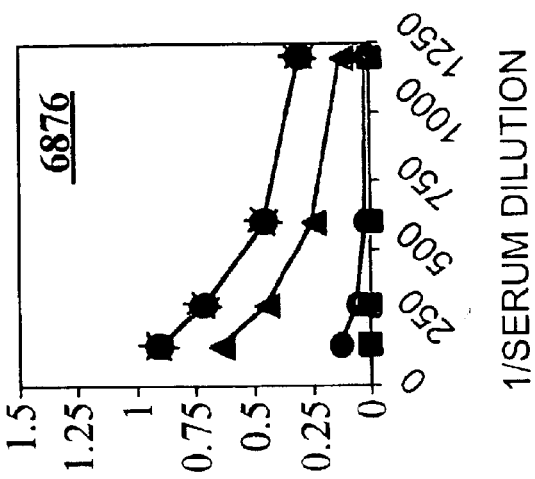
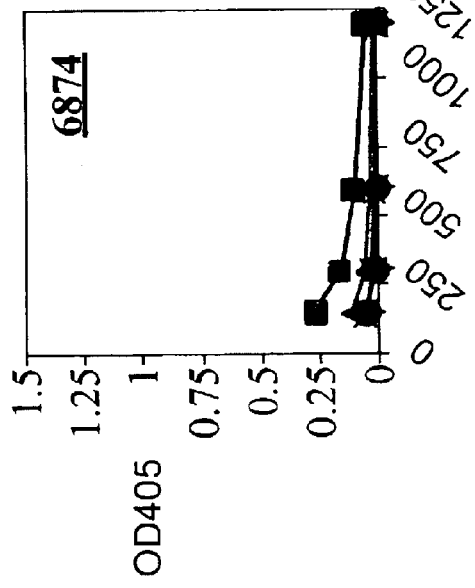

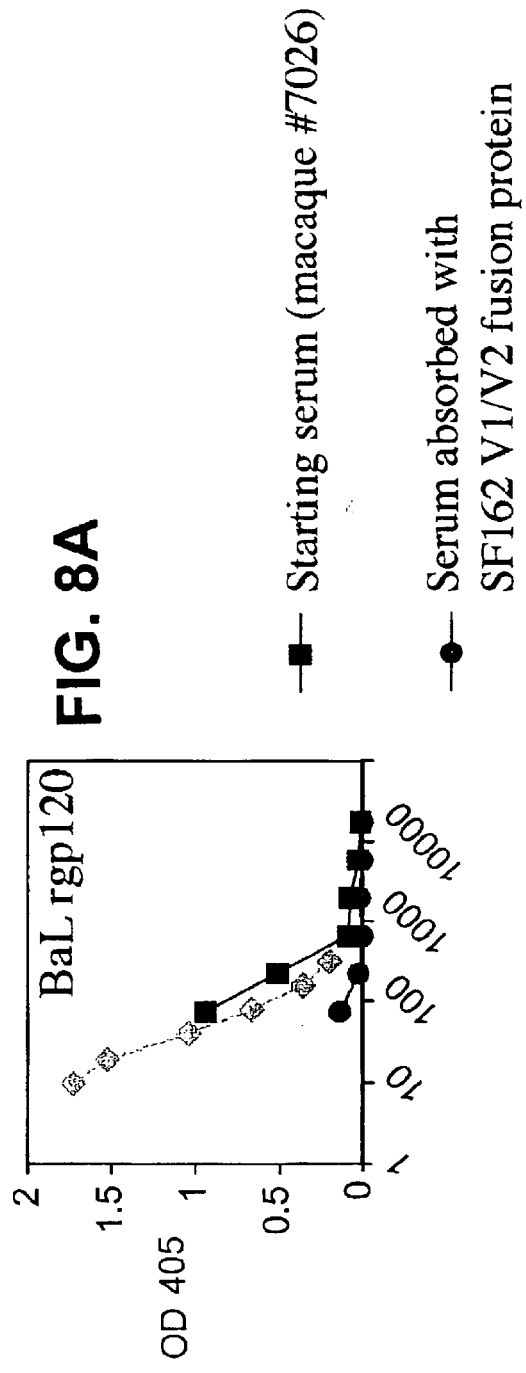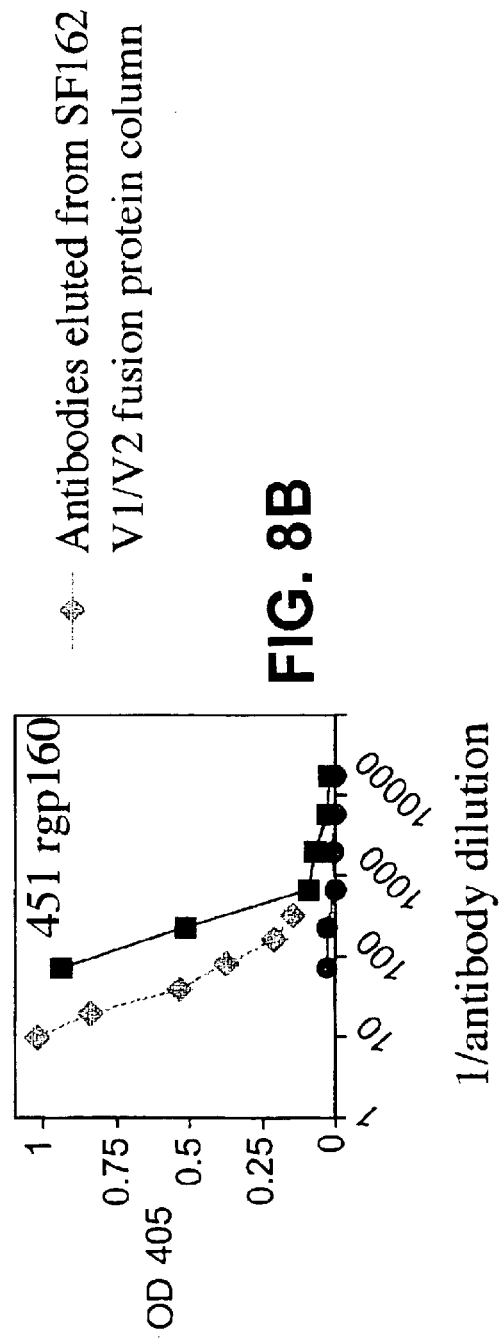
FIG. 8A · Starting serum (macaque #7026) · Serum absorbed with SF162 V1/V2 fusion protein · Antibodies eluted from SF162 V1/V2 fusion protein column
FIG. 8B

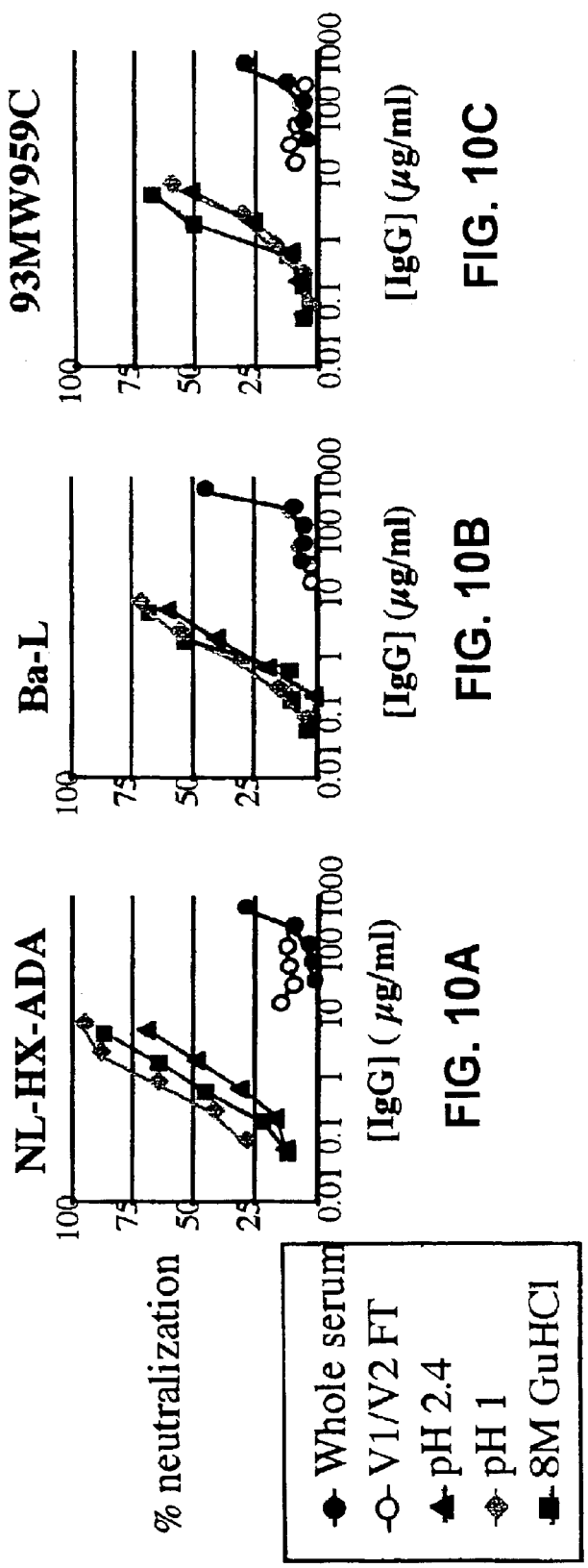

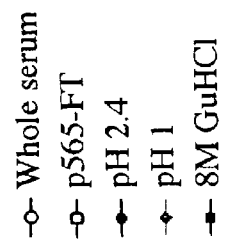
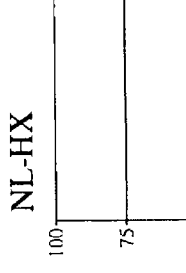
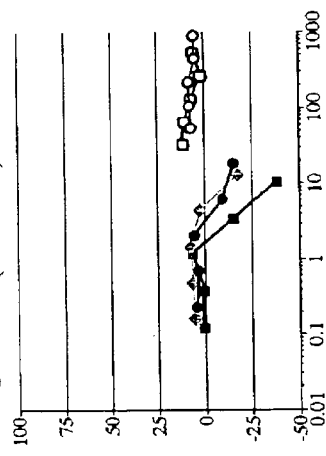
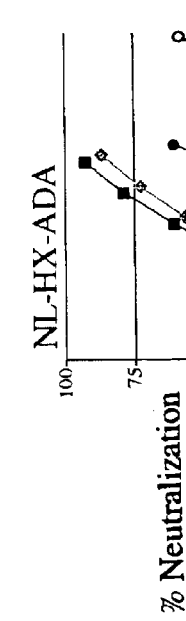
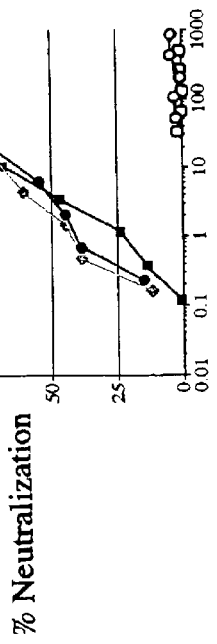
FIG. 12A  FIG. 12B  FIG. 12C  FIG. 12D "V1/V2 stem-only"

HIV-1 GP120 V1/V2 DOMAIN EPITOPES CAPABLE OF GENERATING NEUTRALIZING ANTIBODIES

This application is a continuation of application Ser. No. 09/508,208, now abandoned, which is the National Stage of International Application No. PCT/US98/18679, filed Sep. 8, 1998, which claims the benefit of U.S. Provisional Patent Application No. 60/058,155, filed 8 Sep. 1997.

BACKGROUND OF THE INVENTION

There is presently a dearth of candidate HIV vaccines that are considered suitable for wide-scale testing in humans, particularly when considering vaccines capable of inducing protective humoral immunity. Whereas live, attenuated viruses may provide protection against more pathogenic strains, safety considerations are likely to preclude the widespread use of such vaccines. A difficulty with purified envelope subunit vaccines is that while the best of these have been able to induce neutralizing responses against the vaccine strain and related laboratory-adapted, T cell-tropic HIV-1 strains, these vaccines have generally not induced neutralizing responses to primary viruses and clinical HIV-1 isolates (Hanson, 1994; Mascola et al., 1994; Matthews, 1994). This finding may be related to the general resistance of primary viruses to neutralization by sCD4 (Ashkenazi et al., 1991; Gomatos et al., 1990), monoclonal antibodies (D'Souza et al., 1995; Moore et al., 1995), and immune sera from many HIV-infected patients (Golding et al., 1994). The reason for the difference in sensitivities of primary viruses and lab isolates is not clear. It has been suggested that epigenetic factors related to the cells used to prepare the virus (Sawyer et al., 1994) and to the incorporation of host cell adhesion proteins into virion membranes (Guo and Hildreth, 1995; Hildreth and Orentas, 1989) may be involved, but it appears that structural differences in the envelope proteins of the different viruses may also be important.

Whereas it is known that some people possess potent neutralizing antibodies against primary strains of HIV, such activities are rare. Moreover, the nature of the epitopes that mediate this activity are generally unknown. A major difference between the immune responses of naturally infected individuals and those vaccinated with envelope subunit proteins is that while the humoral responses of the former are directed mostly against conformational epitopes on the viral envelope proteins that are well exposed on native virions (Moore and Ho, 1993), antibodies produced by vaccination with envelop subunit proteins are directed primarily against linear epitopes that are poorly accessible on both monomeric and cell-associated gp120 molecules (VanCott et al., 1995). The natural immune response against HIV-1 has been characterized by isolation and characterization of monoclonal antibodies (mabs) from infected individuals. These studies have utilized cell-adapted laboratory strains of HIV-1, and the mabs that have been described all have preferential neutralizing activity for lab strains over primary viruses. The major neutralization targets recognized in these studies were the V3 loop and the CD4-binding site (Chamat et al., 1992; D'Souza et al., 1994; Gorny et al., 1993; Thali et al., 1992; Tilley and Pinter, 1993).

Whereas it has been reported that some anti-V3 mabs can neutralize primary viruses (Conley et al., 1994), such neutralization is relatively inefficient, requiring 10–100 ug/ml of antibody (D'Souza et al., 1995), considerably more than that required for neutralization of susceptible lab strains. Consistent with these findings are results showing that depletion of anti-V3 antibodies from a human serum resulted in loss of neutralizing activity against the T cell-tropic MN strain, but not against several primary isolates (VanCott et al., 1995). This may be related to other evidence showing that the V3 loop in primary viruses may be buried, and not readily accessible to neutralizing antibodies (Bou-Habib et al., 1994).

A number of human mabs described in the above studies compete for binding of CD4 and have potent neutralizing activities for lab strains of HIV (Cordell et al., 1991; Ho et al., 1991; Tilley et al., 1991). These mabs are directed against conserved, conformational epitopes that are composed of residues scattered over many conserved regions of gp120 (Thali et al., 1992), including residues essential for binding of CD4 itself (Olshevsky et al., 1990). Primary viruses are much less sensitive to neutralization by these mabs than lab strains (Honnen et al., 1996; Moore et al., 1995), similar to their resistance to sCD4 itself, and there have been reports that in some cases these antibodies actually enhance infection by primary HIV-1 isolates (Lee et al., 1997; Schutten et al., 1995; Stamatatos et al., 1997). Several human mabs against other Env epitopes have been identified that have better neutralizing activities for primary isolates (Trkola et al., 1995). These include IgG b12, an anti-CD4-binding site human mab isolated from a combinatorial phage library (Burton et al., 1994), 2F5, directed against a linear epitope in gp41 (Conley et al., 1994; D'Souza et al., 1995; Muster et al., 1994; Trkola et al., 1995), and 2G12, directed against a poorly defined, glycan-dependent epitope in gp120 (Fouts et al., 1997; Trkola et al., 1996). The ability of all three of these mabs to neutralize primary viruses is a reflection of their overall increased potencies, but they also appear to have preferential activity for lab strains over primary viruses (Honnen et al., 1996).

Several studies document the role of the V1/V2 domain as a major antigenic target for HIV-1. A number of rodent mabs have been isolated from animals immunized with recombinant IIIB gp120 that are directed against linear (Fung et al., 1992) and conformational epitopes in the V2 domain (Ho et al., 1991; McKeating et al., 1993; Moore et al., 1993). HIV-infected humans have been shown to produce antibodies against linear epitopes located in both the V2 (Kayman et al., 1994; McKeating et al., 1993; Moore et al., 1993) and V1 regions (Honnen et al., 1996; Pincus et al., 1994). The linear V1 epitopes and some of the linear V2 epitopes mediate type-specific neutralization of IIIB virus and related lab strains.

Many of the anti-V2 neutralizing antibodies that have been described are directed against type-specific epitopes and appear to possess weak neutralizing activities. Thus, the significance of these antibodies for in vivo protection is unclear. Recently, however, several primate mabs have been described which have more interesting neutralizing properties. Particularly strong evidence for the role of the V1/V2 domain in neutralization of HIV-1 comes from recent studies with chimpanzee mab C108G, an antibody directed against a glycan-dependent epitope in V2 (Honnen et al., 1996; Vijh-Warrier et al., 1996; Warrier et al., 1994; Wu et al., 1995). This antibody possesses extremely potent neutralizing activities for both lab strains and primary isolates bearing the C108G epitope, including NL-HX-ADA, a primary-like, macrophage-tropic isolate.

SUMMARY OF THE INVENTION

The invention features a protein which includes a gp120 V1/V2 domain of an HIV-1 strain (or a variant or portion thereof) and not a gp120 V3 domain of an HIV-1 strain, which protein does not substantially bind CD4. For purposes of this invention, the V1/V2 domain is also intended to include the immediate conserved flanking sequences that form the conserved stem of the V1/V2 region. The gp120 V1/V2 domain of the protein displays an epitope which is recognized by an antibody which neutralizes at least one HIV-1 primary isolate with a $ND_{90}$ of less than 100 µg/ml. Useful V1/V2 domains include those of strain Case-A2B and strain SF162. Also included in the invention are fragments and derivatives of the V1/V2 region, including V1/V2 stem analogs in which a GAG triplet is inserted between the ends of the C1 and C2 regions (FIG. 13) and V1/V2 proteins containing deletions of various portions of the V1, V2 or the conserved flanking sequences. Such analogs can be based on any desired V1/V2 loop sequence (e.g., Case-A2B or SF162).

In various embodiments: the V1/V2 domain epitope is recognized by an antibody which neutralizes at least at least one HIV-1 primary isolate from each of at least two different clades with a $ND_{90}$ of less than 100 µg/ml; the two different clades are selected from the group consisting of lade A, lade B, lade C, lade D, and clade E; the V1/V2 domain epitope is recognized by an antibody which neutralizes at least two HIV-1 primary isolates of the same lade with a $ND_{90}$ of less than 100 µg/ml; the V1/V2 domain epitope is recognized by an antibody which neutralizes at least one HIV-1 primary isolate of at least three different clades selected from the group consisting of lade A, lade B, lade C, lade D, and lade E, with a $ND_{90}$ of less than 100 µg/ml; the $ND_{90}$ is less than 50 µg/ml; the $ND_{90}$ is less than 20 µg/ml; the $ND_{90}$ is less than 10 µg/ml; the $ND_{90}$. is less than 5 µg/ml; the $ND_{90}$ is less than 1 µg/ml; the V1/V2 domain includes a region that is at least 50%, 75%, or 90% identical to GEIKNCSFNITT-SIRDKVQKEYALFY KLDIVPID; the V1/V2 domain is at least 50%, 75%, or 90% identical to VKLTPLCVTLNCIDL-RNATNATSNSNTTNTTSSSGGLMMEQGEIKNCS FNITTSIRDKVQKEYALFYKLDIVPIDN-PKNSTNYRLISCNTSVITQA (SEQ ID NO: 1); the protein is at least 50%, 75%, or 90% identical to LKPCVKLT-PLCVTLHCTNLKNATNTKSSNWKEMDR-GEIKNCSFKVTTSIRNKMQKEY ALFYKLDV-VPIDNDNTSYKLINCNTSVITQACPKVS (SF162 V1/V2 loop, including 16 amino acids of the C1 flanking region, and 14 amino acids of the C2 flanking region); and the protein is a glycoprotein.

The invention also features a protein which includes a gp120 V1/V2 domain related region that is at least 50% identical to VKLTPLCVTLNCIDLRNATNATSNS NTT-NTTSSSGGLMMEQGEIKNCSFNITT-SIRDKVQKEYALFYKLDIVPIDNPKNS TNYRLIS-CNTSVITQA (SEQ ID NO: 1) and not a gp120 V3 domain of an HIV-1 strain, which protein does not substantially bind CD4, the gp120 V1/V2 domain related region displaying an epitope which is recognized by an antibody which neutralizes at least one HIV-1 primary isolate with a $ND_{90}$ of less than 100 µg/ml.

The invention also features a protein which includes a gp120 V1/V2 domain of an HIV-1 strain and not a gp120 V3 domain of an HIV-1 strain, which protein does not substantially bind CD4. The protein, when used to immunize a rat, being capable of eliciting an antibody which neutralizes at least one HIV-1 primary isolate with a $ND_{90}$ of less than 100 µg/ml. In various preferred embodiments the antibody elicited neutralizes at least two HIV-1 primary isolates, at least two HIV-1 primary isolates of two different clades (e.g., clade A, clade B, clade C, clade D, and clade E).

The invention also features a monoclonal antibody which binds the gp120 V1/V2 domain of HIV-1 strain Case-A2 and neutralizes at least one HIV-1 primary isolate with a $ND_{90}$ of less than 100 µg/ml. In various preferred embodiments the antibody neutralizes at least two HIV-1 primary isolates, at least two HIV-1 primary isolates of two different clades (e.g., clade A, clade B, clade C, clade D, and clade E)

The invention also features a method for stimulating the formation of antibodies capable of neutralizing infection by an HIV viral isolate in at least one mammalian species, which method includes immunizing a mammalian subject with a composition comprising a protein which includes a gp120 V1/V2 domain of an HIV-1 strain and not a gp120 V3 domain of an HIV-1 strain, which protein does not substantially bind CD4. The gp120 V1/V2 domain of the protein displays an epitope which is recognized by an antibody which neutralizes at least one HIV-1 primary isolate with a $ND_{90}$ of less than 100 µg/ml.

In various embodiments the composition is suspended in a pharmaceutical carrier or vehicle; the composition comprises an adjuvant; such as an aluminum salt or an oil-in-water emulsion comprising a emulsifying agent and a metabolizable oil; or an immunostimulating agent and the composition is administered to the mammalian subject by injection.

It may be desirable to administer combination vaccines having one component that elicits an immune response primarily against macrophage-tropic HIV strains and a second component that elicits an immune response primarily against T Cell-tropic HIV strains. It may also be desirable for either or both components to be composed of a mixture of antigens, e.g., a mixture of antigens each of which elicits an immune response to a particular HIV strain or group of HIV strains.

The invention also includes a hybrid protein having a first part and a second part, the first part including a protein which includes a gp120 V1/V2 domain of an HIV-1 strain (or a variant thereof) and not a gp120 V3 domain of an HIV-1 strain, which protein does not substantially bind CD4, the second part including an amino terminal carrier protein comprising all or a portion of Friend MuLV gp70, preferably amino acids 1–33 or 1–263 of gp70 and, optionally, a His6 tag. The fusion protein can also include a specific cleavage site (ENLYFQS or ENLYFQG) for TEV protease (rTEV protease; Gibco, Bethesda, Md.) immediately preceding the V1/V2 region. TEV protease cleaves its specific cleavage site between the Q and S or G residues. The fusion protein can be purified on a Ni-NTA column if a His6 tag is present or by other suitable means. After digestion with TEV protease (50 U/ml at RT for 18 h) the mixture is passed over a second Ni-NTA column to remove the gp70 carrier (and TEV protease, which also carries a His6 tag). Free V1/V2 domain is recovered in the flow-through fraction.

As used herein, the term "transfected cell" means any cell into which (or into an ancestor of which) has been introduced, by means of recombinant DNA techniques, a nucleic acid encoding a polypeptide of the invention.

As used herein, both "protein" and "polypeptide" mean any chain of amino acid residues, regardless of length or post-translational modification (e.g., glycosylation or phosphorylation). The polypeptides of the invention are referred to as "substantially pure," meaning that they are at least 60% by weight (dry weight) the polypeptide of interest. Preferably, the polypeptide is at least 75%, more preferably at least 90%, and most preferably at least 99%, by weight, the polypeptide of interest. Purity can be measured by any appropriate standard method, e.g., column chromatography, polyacrylamide gel electrophoresis, or HPLC analysis. The polypeptide can be a naturally occurring, synthetic, or a recombinant molecule consisting of a hybrid with one portion, for example, encoding all or a portion of a V1/V2 domain, and a second portion being encoded by all or part of a second gene.

In the context of a polypeptide or protein, the term "substantially identical," refers to a polypeptide having a sequence that is at least 85%, preferably at least 90%, more preferably at least 95%, and most preferably at least 98% or 99% or more identical to the amino acid sequence of the reference polypeptide. For polypeptides, the length of the reference polypeptide sequence will generally be at least 16 amino acids, at least 20 amino acids, at least 25 amino acids, or preferably at least 35 amino acids. For nucleic acids, the length of the reference nucleic acid sequence will generally be at least 50 nucleotides, at least 60 nucleotides, at least 75 nucleotides, or at least 90 nucleotides.

Sequence identity can be measured using sequence analysis software (e.g., Sequence Analysis Software Package of the Genetics Computer Group, University of Wisconsin Biotechnology Center, 1710 University Avenue, Madison, Wis. 53705) with the default parameters specified therein.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

The members of a pair of molecules (for example, an antibody-epitope pair or a receptor-ligand pair) are said to "specifically bind" to each other if they bind to each other with greater affinity than to other molecules. Thus, an antibody which specifically binds to a particular epitope within a V1/V2 domain binds to that particular V1/V2 domain epitope with greater affinity than to other V1/V2 domain epitopes.

The amino acid sequences of many HIV-1 gp120 protein are described in Meyers et al. (1996).

The V1/V2 domain is that region of HIV-1 gp120 which corresponds to the following sequence from Case-A2 gp120: VKLTPLCVTLN CIDLRNATNATSNSNTTNTTSSSGGLMMEQGEIKN CSFNITTSIRD KVQKEYALFYKLDIVPI DNPKNST-NYRLISCNTSVITQA (SEQ ID NO: 1) Other V1/V2 domains can be identified by aligning SEQ ID NO: 1 with a gp120 sequence using standard sequence alignment software. Myers et al. (1996) provides alignments of a number of gp120 proteins. The four Cys residues underlined in SEQ ID NO:1 are essentially invariant and can-be used to assist in alignment. Other important highly conserved residues are the underlined Ser, Phe, Ala, and Asp residues. It should be noted that the V1/V2 domain defined above extends somewhat beyond the V1 and V2 loops as defined in Myers et al. (1996).

The "V3 domain" of gp120 is that region identified in Myers et al. (1996) as the V3 loop.

A protein which does not substantially bind to CD4 is a protein which does not show appreciable binding of CD4 when tested in a CD4 binding assay such as that described in U.S. Pat. No. 5,653,985.

The antigenic peptides described herein are useful in vaccine compositions or compositions used to elicit a humoral immune reponse. They may also be used in immunoassays for anti-HIV antibodies and for the production of anti-HIV antiserum.

The invention encompasses nucleic acid molecules encoding the proteins of the invention. Nucleic acid molecules within the invention can be cDNA, genomic DNA, synthetic DNA, or RNA, and can be double-stranded or single-stranded (i.e., either a sense or an antisense strand). Fragments of these molecules, which are also considered within the scope of the invention, can be produced, for example, by the polymerase chain reaction (PCR) or generated by treatment with one or more restriction endonucleases. A ribonucleic acid (RNA) molecule can be produced by in vitro transcription.

The preferred methods and materials are described below in examples which are meant to illustrate, not limit, the invention. Skilled artisans will recognize methods and materials that are similar or equivalent to those described herein, and that can be used in the practice or testing of the present invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the detailed description, and from the claims.

BRIEF DESCRIPTION OF THE DRAWINGS

FIG. 1: Comparison of the sequence of HIV-1 Case A2 gp120 and HIV-1 HXB2 gp120 between residues 158 and 185 to the most common and second most common residues found at these positions in 55 clade B strains. The frequency of occurrence of a particular residues is shown below the consensus sequences.

Figure 2:
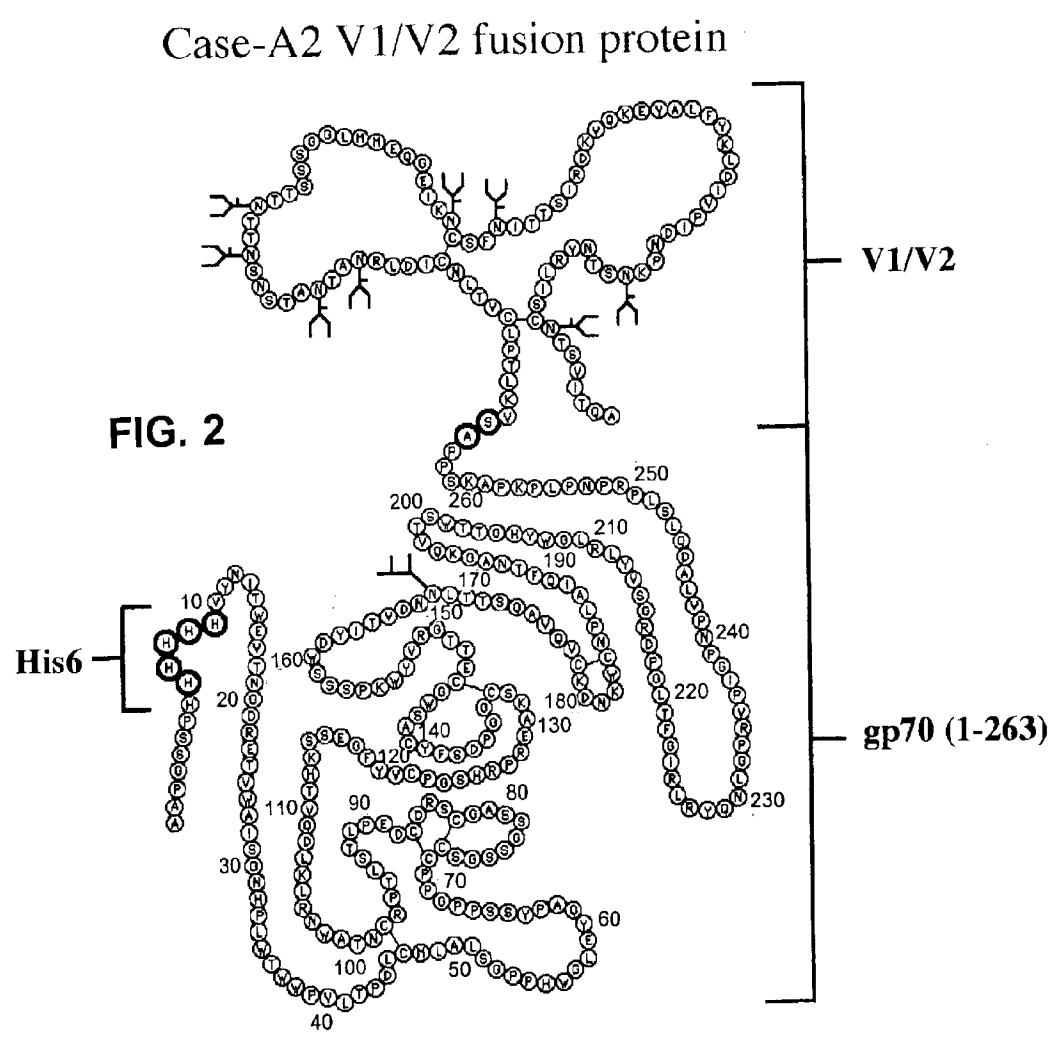

FIG. 2: Proposed structure of the Case A2 fusion protein. Amino acids 111–206 of the HIV-1 Case A2 gp120 V1/V2 domain were fused to the C-terminus of a 263 amino acid N-terminal fragment of MULV gp70 protein. The Q residue at position 9 of MuLV gp70 was replaced by five His residues to provide an affinity tag to facilitate purification of the fusion protein.

FIG. 4A: Neutralization of Bal (squares; ND=0.24 $\mu$g/ml), NHA (diamonds; $ND_{50}$=0.096 $\mu$g/ml), ADA (circles; $ND_{50}$= 0.058 $\mu$g/ml), Th014B (upward pointing triangles; $ND_{50}$= 0.14 $\mu$g/ml), Ug/005D (downward pointing triangles; $ND_{50}$= 0.03 $\mu$g/ml), and Th024E (crosses; $ND_{50}$=n.d.) by antibodies eluted from the Case-A2 fusion protein affinity column with the 5M GuHCl wash.

FIG. 4B: Neutralization of Bal (squares; $ND_{50}=12.0$ µg/ml), NHA (diamonds; $ND_{50}=9.9$ µg/ml), ADA (circles; $ND_{50}=3.2$ µg/ml), Th014B (upward pointing triangles; $ND_{50}=0.86$ µg/ml), Ug/005D (downward pointing triangles; $ND_{50}=<0.8$ µg/ml), and Th024E (crosses; $ND_{50}=3.8$ µg/ml) by antibodies eluted from the T15K peptide affinity column with the pH 3 wash.

FIGS. 5B, 5C, and 5D) or gp70 carrier protein (p621; FIG. 5A). Sera were obtained two weeks after a second immunization and tested by direct ELISA against gp70 carrier protein (open squares), Case-A2 fusion protein (closed squares), Thai clade E (p580, Tho6.05E) V1/V2 fusion protein (circles), Brazilian clade B (p599, 92Br14.01B) V1/V2 fusion protein (triangles), and T15K peptide (cross-hatched squares).

FIGS. 7A–7C: Cross reactivity of sera from macaques 6874 (FIG. 7A), 6876 (FIG. 7B), and 7026 (FIG. 7C) with gp70 carrier protein (closed squares), NA consensus clade B sequence (closed diamonds), Brazil clade B V1/V2 protein (closed triangles), and Thai clade E V1/V2 protein (closed circles).

FIGS. 8A and 8B: Crossreactivity of BaL recombinant gp120 (FIG. 8A) and 451 recombinant gp160 (FIG. 8B) with serum from macaque 7026 (closed squares), macaque 7026 serum absorbed with SF162 V1/V2 fusion protein (closed circles), and antibodies eluted from a SF162 V1/V2 fusion protein column (closed diamonds).

FIGS. 10A–10C: Neutralization of NL-HX-ADA (FIG. 9A), Ba-L (FIG. 10B) and 93MW959C (FIG. 10C) by macaque 7026 whole serum (closed circles; line), V1/V2 flow through (closed circles; no line), pH 2.4 wash (closed triangles), pH 1 wash (closed diamonds), and 8M GuHCl wash (closed squares).

FIGS. 12A–12D neutralization of two macrophage-tropic isolates, NL-HX-ADA (FIG. 12A) and Case-A2 NL-HX-ADA (FIG. 12B), and two T cell-tropic isolates, NL-HX (FIG. 12C) and Case A2 NL-HX (FIG. 12D) by macaque serum fractions. Fractions tested included: p565 flow through (open squares), pH 2.4 wash (closed circles) pH 1 wash (closed triangles), and 8M GuHCl wash (closed rectangles). Whole serum was also tested (closed squares).

DETAILED DESCRIPTION OF THE INVENTION

Proteins Which Elicit Highly Neutralizing Antibodies

Figure 3:
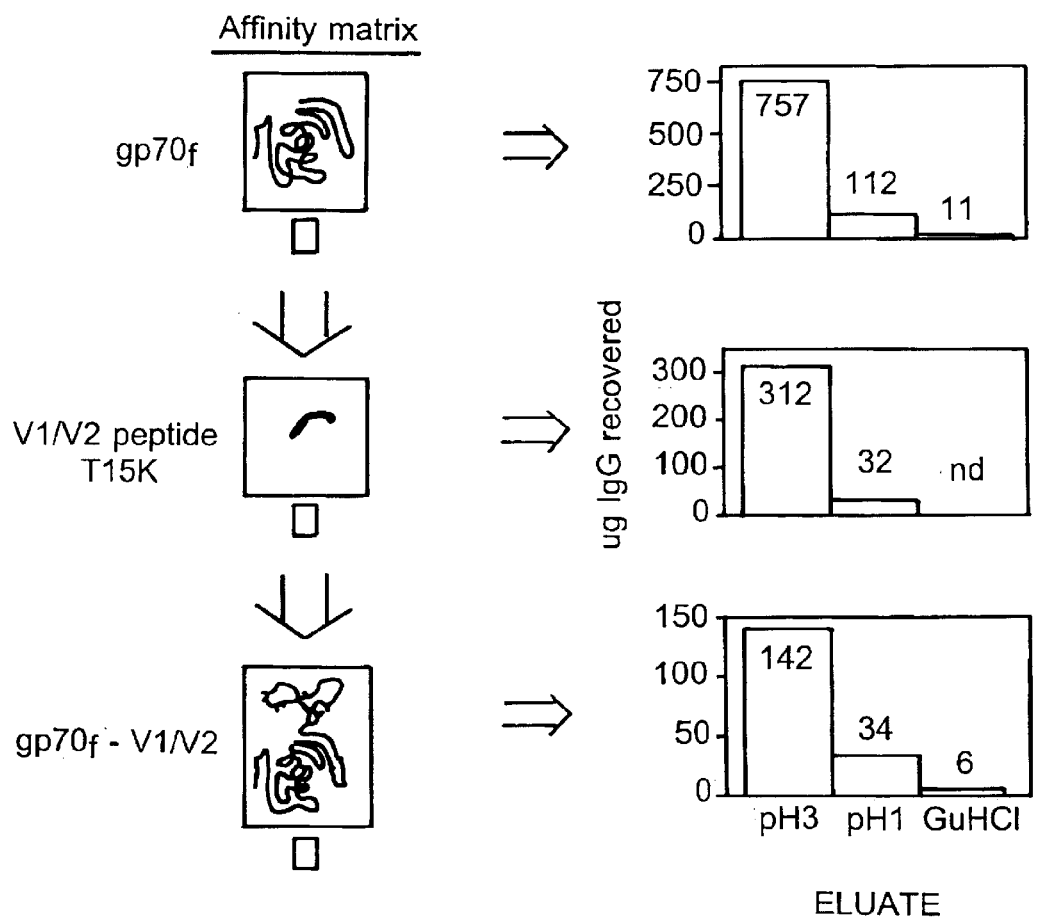
FIG. 3: Schematic illustration of the serum fractionation protocol. The three affinity columns used in the serum fractionation protocol are shown at the left. Just to the right of each column is a graph illustrating the amount of antibody recovered by each wash of the corresponding column.
Figure 5A:
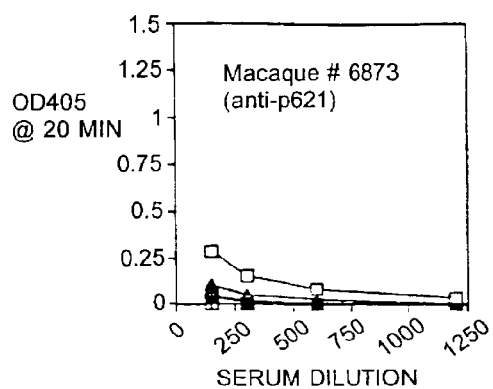
FIGS. 5A–5D: Cross-clade immunoreactivity of sera of macaques immunized with Case-A2 fusion protein (p565.
Figure 5B:
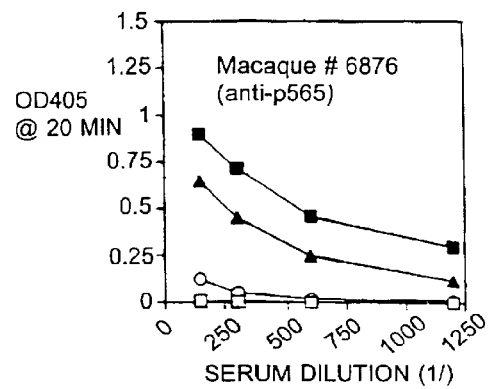
Figure 5C:
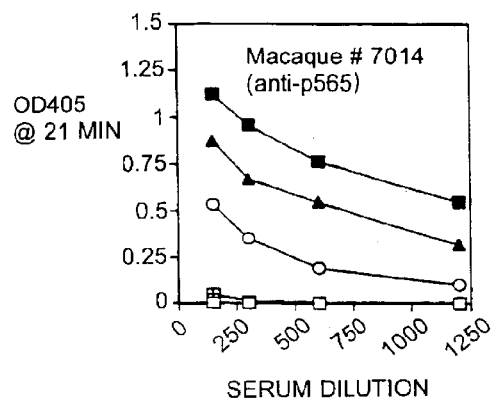
Figure 5D:
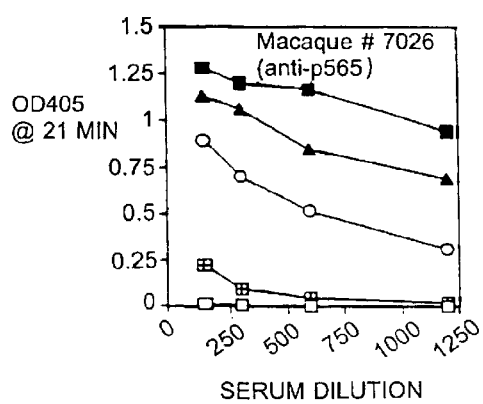

The proteins of the present invention display conformational epitopes which elicit highly neutralizing antibodies capable of neutralizing primary HIV-1 isolates. Preferred proteins are those which can elicit antibodies which neutralize primary isolates in two or more different clades (e.g., two or more of clades A, B, C, D, and E).

The proteins of the present invention can exist in a is variety of different conformations. Thus, when a protein composition is said to comprise a protein which express a particular epitope, it does not mean that every protein molecule in the composition displays that particular epitope. A protein of a given sequence can exist in a variety of conformations, and a variety of conformations are likely to be present in any composition containing a given protein. The proteins of the invention are expressed and isolated such that at least 10%, preferably 20%, 50%, 70%, or even 90% of the protein molecules display the desired epitope.

Case-A2 gp120 V1/V2 Domain Fusion Protein Elicits Highly Neutralizing Antibodies The studies described below demonstrate that a fusion protein containing the V1/V2 domain of gp120 derived from the Case-A2 clinical HIV-1 isolate can generate highly neutralizing antibodies when used to immunize rats. Significantly, the fusion protein can generate antibodies that neutralize a number of primary macrophage-tropic HIV strains. Moreover, the fusion protein can generate antibodies which neutralize primary HIV isolates of several different clades.

The fusion protein containing the V1/V2 domain of gp120 used in the studies described below (the "Case-A2 fusion protein") consists of residues 111–206 of the gp120 protein of the Case A2 isolate of HIV-1 (Wang et al., 1995) joined to the C-terminus of residues 1–263 of MULV gp70 protein (Kayman et al., 1994). For ease of purification, a His6 affinity tag was inserted into residues 1–263 of MuLV gp70 by replacing the Q residues at position 9 with five His residues. The Case-A2 V1/V2 domain has the following sequence: VKLTPLCVTLNCIDLRNATNATSNSNTT-NTTSSSGGLMMEQGEIKNCSFNITTSIRD KVQKEY-ALFYKLDIVPI DNPKNSTNYRLISCNTSVITQA (SEQ ID NO: 1)

To create a Case-A2 fusion protein expression vector, a recombinant gene encoding the Case-A2 fusion protein was inserted into the pEE14 expression vector (Celltech Limited, Berkshire, UK). This construct contains two extraneous amino acids (AS) between the gp70 and V1/V2 sequences and two extraneous amino acids (GA) after the C-terminus of the V2 region. This expression vector also expresses the glutamine synthetase gene, which allows selection of transfected cells by growth in glutamine-deficient medium in the presence of methionine sulfoxamine (MSX), a glutamine antagonist (Bebbington et al., 1992). The Case-A2 fusion protein expression vector was transfected into CHO cells, and transfected clones were isolated in the selecting medium (glutamine-free RPMI containing 10% dialyzed fetal bovine serum and 80 µM MSX). Clones expressing the Case-A2 fusion protein were identified by ELISA using mab 238, directed against a conformational epitope in V2 (Moore et al., 1993). Proteins secreted by several positive clones were analyzed by radioimmunoprecipitation and SDS-PAGE.

Figure 6:
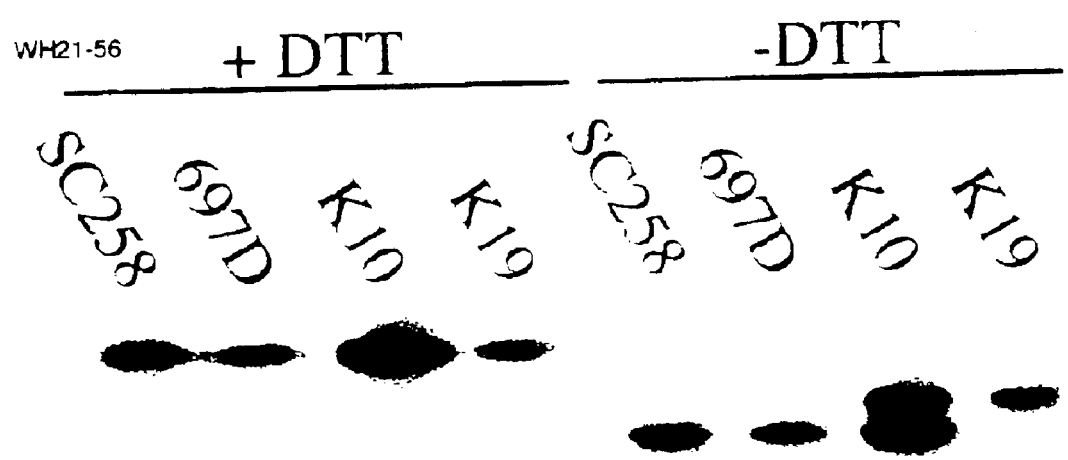
FIG. 6: SDS-PAGE analysis of two distinct conformational forms of Case-A2 fusion protein. Radiolabeled supernatant of cells producing the Case-A2 V1/V2 fusion protein were immunoprecipitated with the indicated antibodies and subjected to PNGase F deglycosylation prior to SDS-PAGE.
Figures 9A, 9B, 9C:
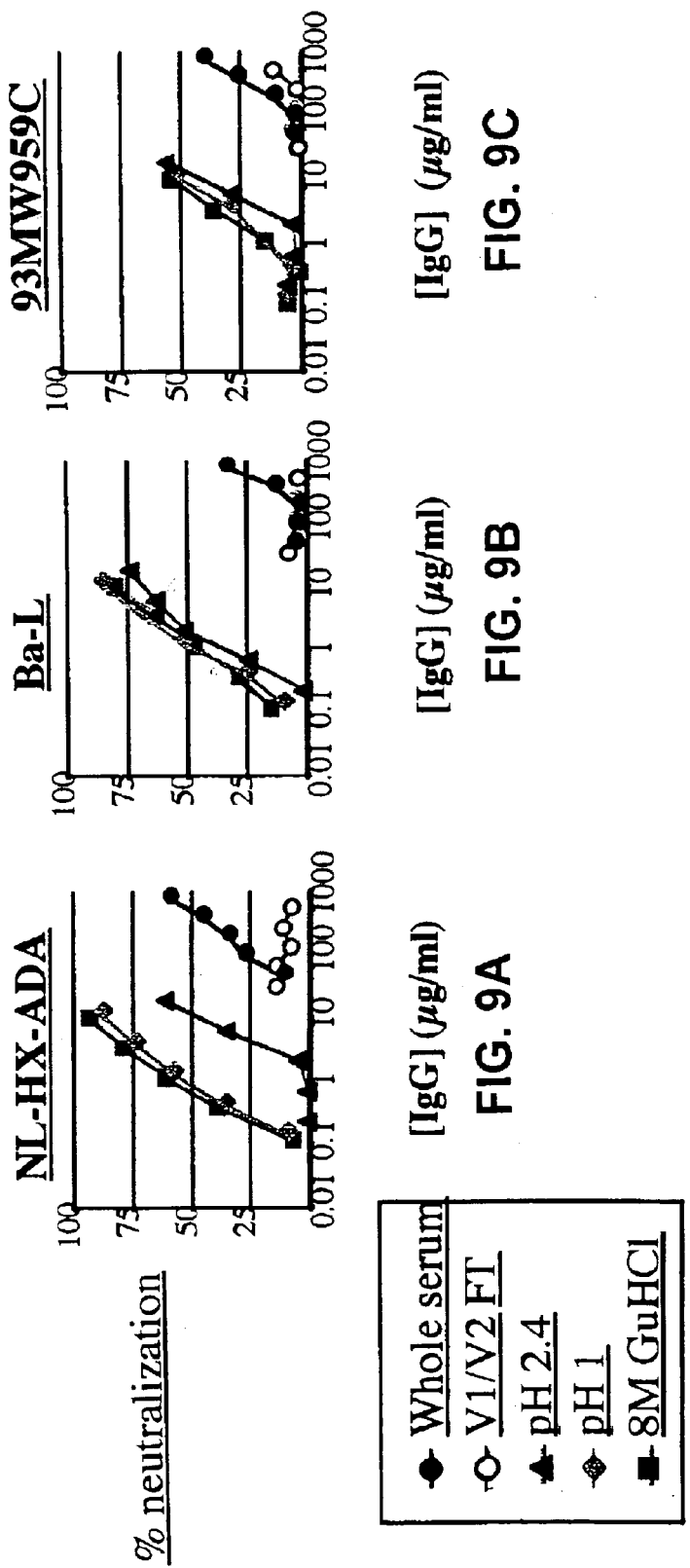
FIGS. 9A–9C: Neutralization of macrophage-tropic HIV-1 strains NL-HX-ADA (FIG. 9A), Ba-L (FIG. 9B) and 93MW959C (FIG. 9C) by macaque 6876 whole serum (closed circles; line), V1/V2 flow through (closed circles; no line), pH 2.4 wash (closed triangles), pH 1 wash (closed diamonds), and 8M GuHCl wash (closed squares).

Analysis of the Case-A2 fusion protein produced as described above revealed that the protein exists in at least two forms which can be distinguished by their reactivity with different monoclonal antibodies. A monoclonal antibody K19B3, isolated from rats immunized with the Case-A2 fusion protein, recognized approximately half of the fusion protein molecules while a second monoclonal antibody, SC258 (obtained from Abbott Labs) directed against conformational V2 epitopes (Wu et al., 1995), reacted predominantly with the other half of the fusion protein molecules. This suggests that about half of the molecules were correctly folded and presented native conformational epitopes, while the other half of the molecules may be misfolded and present linear or misfolded epitopes (FIG. 6).

Immunizations of Rats with Case-A2 Fusion Protein

A number of 2–4 month old female Fischer F344 rats were immunized with purified Case A2 fusion protein or HXB2 fusion protein. HXB2 fusion protein was created in the same manner as the Case A2 fusion protein except that the V1/V2 domain portion of the fusion protein has the sequence of the HXB2 HIV-1 isolate rather than the Case A2 isolate (FIG. 1).

The fusions proteins were combined with either QS21 (from CBCX, Inc. Worcester, Mass.) or RAS MPL+TDM (Ribi Immunochemicals, Inc. Hamilton, Mo.) adjuvant according to the manufacturer's instructions. Three rats in each group were immunized with immunogens at 5 µg/rat and were boosted using the same formulation 6 weeks later at 1 µg/rat. Rats were then boosted at a 5–6 week intervals using the same formulation at 1 µg/rat. Rats were bled one week after each boost. Serum was analyzed by ELISA using various antigens. The ELISA analysis revealed that the Case A2 fusion protein is a more effective immunogen than the HXB2 fusion protein. Sera from both RAS and QS21 adjuvant groups were analyzed for their cross-reactivity against purified envelope proteins derived from LAV, MN, and CM strains, using equal amounts of each envelope protein. In general, rats immunized with Case-A2 fusion protein produced higher titers and better cross-reactivity than those immunized with HXB2 fusion protein. All three-rats immunized with Case-A2 fusion protein produced antibodies that cross-reacted with LAV gp120, and several of the immunized animal sera demonstrated appreciable titers to MN and BaL gp120s. These results indicated that despite the purported hypervariability of the V1/V2 region, the Case-A2 fusion protein is able to generate antibodies with significant titers against several unrelated gp120 with heterologous V1/V2 sequences. Furthermore, since the gp120s used were produced in CHO cells, they are likely to be properly glycosylated and folded. Thus, it appears that cross-reactive anti-V1/V2 antibodies produced by rats immunized with Case A2 fusion protein recognize conserved, native epitopes within the V1/V2 domain of gp120.

Epitope Specificity of Anti-V1/V2 Antibodies Elicited by Case-A2 Fusion Protein

Western blots assays indicated that the sera of some rats immunized with the V1/V2 fusion proteins contained antibodies that reacted with epitopes in the V1/V2 fusion proteins that are not dependent on the maintenance of disulfide bonds. In order to map the epitopes in the Case-A2 sequence recognized by these antibodies, a set of overlapping 15-mer peptides that represent the entire Case-A2 V1/V2 sequence were prepared. ELISA assays with these peptides showed that, for five of seven rats immunized twice with the immunogen, the linear epitopes recognized were localized to a single peptide, p7, that corresponds to the most highly conserved region of the V2 domain (TABLE 1). Two other rats immunized seven times with Case A2 fusion protein also recognized only peptide p7. In contrast, a screen of 100 sera of HIV-infected humans identified only one that reacted with peptide p7. This result suggests that this sequence, while highly conserved, is not very immunogenic when expressed during HIV infection, but is immunogenic when presented in the context of the Case-A2 fusion protein.

TABLE 1

Reactivity of Case A2 Sera to Various V1/V2 Domain Peptides

| Peptide | Sequence | OD$_{405}$ (range) |
|---|---|---|
| p1 | asVKLTPLCVTLNSI (SEQ ID NO:2) | 0.05 (0–0.38) |
| p2 | VTLNCIDLRNATNAT (SEQ ID NO:3) | 0.01 (0–0.09) |
| p3 | ATNATSNSNTTNTTS (SEQ ID NO:4) | 0.01 (0–0.06) |
| p4 | TNTTSSSGGLMMEQG (SEQ ID NO:5) | 0.02 (0–0.16) |
| p5 | MMEQGEIKNCSFNIT (SEQ ID NO:6) | 0.00 |
| p6 | SFNITTSIRDKVQKE (SEQ ID NO:7) | 0.00 |
| p7 | SIRDKVQKEYALFYK (SEQ ID NO:8) | 1.04 (0.39–1.46) |
| p8 | EYALFYKLDIVPIDN (SEQ ID NO:9) | 0.00 |

In order to further characterize the antibodies elicited by Case A2 fusion protein, analogues of peptide p7 were generated. To increase the solubility of the analogues and to facilitate the immobilization of the analogues, two additional lysine residues were introduced at the N-terminus, followed by two naturally occurring threonines. The resulting peptide was called T15K, and has the sequence kkTT-SIRDKVQKEYALFYK (SEQ ID NO:10).

The specificities of the antibodies recognizing this peptide's epitopes were further defined by analyzing a series of N-terminal and C-terminal truncations of peptide T15K peptide (TABLE 2). Peptides that expressed the epitope, as defined by retention of reactivity by the majority of rat sera, were T15K, pep1, pep2, and pep4. Deletion of the C-terminal lysine did not affect the epitope, while deletion of an additional two hydrophobic residues, phenylalanine and tyrosine, resulted in a reduction of binding. Deletion of an additional leucine resulted in loss of recognition by all but one serum. N-terminal deletions of the two threonines retained reactivity, while further deletion of serine and isoleucine led to the complete loss of reactivity of both sera. Thus, the minimal epitopes recognized were located in the sequence (S)IRDKVQKEYAL(FY) (SEQ ID NO:11), with a decreased or unknown effect of the terminal residues in parentheses. Interestingly, this sequence partially overlapped with the homologous peptide determinant (STSIRGKV; SEQ ID NO:12) of the strongly neutralizing C108G MAb (Wu et al., 1995), suggesting that this region may also be a neutralization epitope.

TABLE 2

Epitope Mapping of Antibodies Elicited by Case A2 Fusion Protein

| Peptide | Sequence | OD$_{405}$ (range)* |
|---|---|---|
| C-terminal deletions | | |
| T15KkkTTSIRDKVQKEYALFYK | (SEQ ID NO:13) | 1.34 (0.91–1.92) |
| pep1kkTTSIRDKVQKEYALFY | (SEQ ID NO:14) | 0.86 (0.49–1.53) |
| pep2kkTTSIRDKVQKEYAL | (SEQ ID NO:15) | 0.59 (0.02–1.40) |
| pep2akkTTSIRDKVQKEYA | (SEQ ID NO:16) | 0.35 (0.02–1.38) |
| pep3kkTTSIRDKVQKEY | (SEQ ID NO:17) | 0.23 (0.02–0.81) |
| N-terminal deletions | | |
| pep4kk--SIRDKVQKEYALFYK | (SEQ ID NO:18) | 0.99 (0.02–1.40) |
| pep5kk-----RDKVQKEYALFYK | (SEQ ID NO:19) | 0.24 (0.02–0.94) |
| pep6kk-------DKVQKEYALFYK | (SEQ ID NO:20) | 0.09 (0.02–0.38) |

*Values are average of values obtained with six rat sera. ELISAs were performed with 1:100 serum dilutions Neutralization Activities of Anti-V1/V2 Antibodies Elicited by Case A2 Fusion Protein Preliminary experiments indicated that the sera of all of the immunized rats possessed neutralization activities against a number of HIV-1 isolates. In order to evaluate the role and potency of the anti-V1/V2 antibodies present in these sera, and to eliminate background effects due to nonspecific components present in the sera, the immunoglobulins were sequentially fractionated by affinity chromatography using several different antigen columns (FIG. 3). The serum was first absorbed on a column containing p621, a recombinant protein containing only the gp70-derived sequences (including the His6 tag) present in the fusion protein, to remove the irrelevant anti-gp70 antibodies. The material which did not adhere to this column was applied to a column containing immobilized T15K peptide, and the unabsorbed flow-through of the T15K column was then applied to a column containing immobilized Case A2 fusion protein. Material which bound to the T15K peptide column or to the Case-A2 V1/V2 column were eluted sequentially with low pH buffers and then with the denaturant 5M guanidium hydrochloride (GuHCl), as described below. This permitted the separate isolation of T15K peptide-specific antibodies and antibodies specific for conformational V1/V2 epitopes.

Immunoaffinity columns containing the T15K peptide, the p621 gp70 fragment, or complete Case-A2 V1/V2 fusion protein were prepared by incubating cyanogen bromide-activated Sepharose beads (Pharmacia) at 4 C with PBS solutions containing 2 mg of protein or 4.5 mg of peptide per ml of beads for 24 hrs. Excess binding sites were blocked by treatment with 100 mM pH 8.0 Tris buffer, the beads were washed, and used for antibody fractionations. Sera were diluted five to ten-fold with PBS and shaken overnight with the beads at a ratio of approximately 0.4 ml of serum per ml of beads. The beads were packed into a column, and flow-through containing depleted serum was collected. The column was then washed with PBS and eluted with 10 ml of either pH 2.5 glycine-HCl buffer or sequentially with pH 3.0 and 1.0 glycine-HCl buffers followed by 5–8 M guanidine hydrochloride (GuHCl). The low pH eluates were neutralized immediately with the appropriate volume of 2M tris, pH 9.2 buffer; GuHCl was removed by extensive dialysis against PBS. To stabilize the purified antibodies they were reconstituted to 100% fetal bovine serum; this was done by adding a volume of fetal bovine serum equivalent to the desired final volume and concentrating the sample back to the initial volume of the serum sample, using Centricon-50 spin columns. The eluted antibodies were then analyzed for antigen specificity and for neutralizing activity. In some cases, samples were first run over a control column containing similar amounts of immobilized BSA; this did not result in depletion of any antibody activity or the recovery of specific antibody activity in the eluted fractions.

A total of 1.4 mg of antibody was recovered from the serum of one rat immunized seven times at roughly monthly intervals. Approximately 63% of the antibody was directed against gp70, about 24% was directed against T15K peptide, and about 13% of the antibody was directed against conformational epitopes (i.e., bound tightly only to the Case-A2 column). Interestingly, a similar fractionation of the serum of another rat immunized only twice gave a higher percentage and yield of antibodies against the conserved conformational epitopes, suggesting that the efficiency of these immunizations would be improved by more appropriate timing of boosts.

The neutralizing activities of these samples were compared to those of the starting serum and protein G-purified IgG sample as follows. HIV-1 neutralizations were measured by a fluorescent focus assay, performed in 3 day PHA-activated cultures of human PBMCs grown in complete RPMI-1640 medium supplemented with 10% fetal bovine serum and 50 units recombinant human IL-2/ml (Boehringer Mannheim Inc.). Virus-containing supernatants were preincubated with different dilutions of antibody for 1 hr at 37 C, after which the virus-antibody mixture was added to $5\times10^5$ PBMCs. Neutralizations were measured at times when 2–5% of the cells in the control culture were infected, as determined by assay of the extent of viral spread in control wells; this generally represented an infection period 4–7 days. To assay for infection cells were plated out on polylysine-coated multi-spot slides at a concentration of $1\times10^5$ cells per 5 mm well, the slides fixed with acetone, and the cells stained by incubation with a biotinylated polyclonal IgG purified from human HIV-positive sera by protein A chromatography, followed by FITC-conjugated strepavidin. Infected cells were quantitated by counting fluorescent cells using a Nikon Diophot microscope equipped for epifluorescence. The number of positive cells were determined in five separate areas containing confluent layers of cells (approximately 1,100 cells per area) and all samples were assayed in duplicate wells, so that approximately 11,000 total cells were examined for each point. Reproducibility in viral end points ($ND_{50}s$) was high within single experiments, but variations as much as two-fold in either direction were seen between experiments, particularly when different batches of virus and cells were used.

The antibodies which recognized V1/V2 domain epitopes all possessed potent neutralization activities for a number of primary macrophage-tropic viruses (FIG. 4A and FIG. 4B). The 5M GuHCl eluate of the Case-A2 fusion protein column had the most potent activity (FIG. 4A), but the pH 3 eluate of the T15K also had significant neutralizing activity (FIG. 4B). Both antibody fractions neutralized all primary viruses assayed, including primary isolates of clades B, C, D and E. In each case the anti-Case A2 fusion protein antibody GuHCl eluate fraction was approximately 10-fold more potent that the anti-T15K peptide antibody fraction. Thus, $ND_{50}$ values were in the range of 0.03–0.24 ug/ml for the anti-Case-A2 fusion protein antibody GuHCl eluate fraction (with the exception of Th024E, for which an $ND_{50}$ was not obtained) and in the range of <0.8–12 µg/ml for the anti-T15K peptide antibody fraction. As an example, these antibody fractions neutralized a primary clade D isolate from Uganda, Ug005-D with $ND_{90}$ values of 1.4 ug/ml for the anti-T15K antibody fraction and 0.20 µg/ml for the anti-Case A2 fusion protein antibody GuHCl eluate fraction. In addition to the viruses shown in FIG. 4A, the GuHCl eluate of the Case A2 fusion protein column also neutralized a lade B clinical isolate, US716B, with an $ND_{50}$ of 0.03 µg/ml. The T15K pH 3 eluate also was able to neutralize this virus, but with about an order of magnitude lower potency ($ND_{50}$ of <0.80 µg/ml).

Immunization of Primates

Rhesus macaques can provide an animal model suitable for testing of HIV vaccines. In order to determine whether a primate will produce useful neutralizing antibodies when immunized with Case-A2 fusion protein, three rhesus macaques were immunized with the Case-A2 fusion protein, and one rhesus macaque was immunized with a control immunogen consisting of the gp70-derived portion of the fusion protein, p621. The antigens were formulated with Ribi RAS adjuvant and administered by subcutaneous injection at an initial dose of 25 µg/kg, followed by a boost after 1 month at a dose of 5 µg/kg. Bleeds were taken on the day of and one week after the initial immunization and at weekly intervals following the boost. Antibodies reactive with the immunogen were detected after the first boost. The animal immunized with the p621 produced antibodies specific for the p621 protein, while the three animals immunized with the Case-A2 fusion protein produced antibodies directed against both gp70 portion and the V1/V2 portion of the Case-A2 fusion protein.

These antibodies were further characterized by absorption of the gp70-specific fraction on a gp70 column followed by ELISA against several V1/V2 fusion proteins. As shown in FIGS. 5A–5D, for the animal immunized with the gp70 fragment (p621) the gp70-specific antibodies were all absorbed on an affinity column containing the immobilized p621 protein. For the three animals immunized with the Case A2 fusion protein, the p621 column flow throughs retained reactivity for the V1/V2 portion of the Case A2 fusion protein, but not for p621. All three of these sera recognized two heterologous proteins in addition to the Case A2 sequence, a Brazilian clade protein and a Thai clade E protein (Gao et al., 1994). The titers were higher for the autologous immunogen than for the non-autologous proteins, and lowest for the more distant clade E protein. However, this cross-reactivity demonstrated that these macaques were producing a fraction of antibodies directed against highly conserved V1/V2 epitopes, in addition to antibodies restricted for the Case-A2 and related clade B proteins. Sera from the animal with the highest titer, #7026, also reacted weakly with the TL5K peptide.

Further Characterization of the Case-A2 gp 120 V1/V2 Domain Fusion Protein

Case-A2 fusion protein prepared as described above was purified by affinity chromatography on a Ni-NTA column, utilizing a His6 tag incorporated near the N-terminus of the carrier gp70 sequence. The protein was shown by SDS-PAGE to be >90% pure.

Case-A2 fusion protein exists in at least two conformational forms. A radioimmunoprecipitation analysis of $^{35}$S-cysteine labelled Case-A2 fusion protein demonstrated the presence of two conformational forms of the antigen, which differed both in their reactivity with different monoclonal antibodies and their mobility on SDS gels (approximately 2 kD apparent molecular weight difference) when analyzed under non-reducing conditions (FIG. 6). Both forms were recognized by K10A11, an antibody directed against a site in the gp70-derived carrier domain. The first form (upper band in FIG. 6) was recognized by K19B3, a monoclonal antibody directed against a conserved V1/V2 epitope, while the second form (lower band in FIG. 6) was recognized by SC258 and 697D, mouse and human monoclonal antibody directed against conformational V2 epitopes, as well as by several other mouse and human monoclonal antibodies directed against native conformational epitopes. The second form was also recognized by a number of human sera. This preferential recognition of the second form by the human antibodies suggests that it represents the correctly folded form, while the first form represents an alternative, presumably non-native conformation. The two forms coalesced into one band after reduction of disulfide bonds with DTT, confirming that they represented distinct disulfide-bonded conformers. The two forms were fractionated by affinity chromatography on a column to which monoclonal antibody SC258 was immobilized. The K19-reactive form was present in the flow through, while the native form was eluted by low pH buffer.

Immunization of Rhesus Macaques with Case-A2 Fusion Protein

Three rhesus macaques (6876, 7014 and 7026) were immunized with purified Case-A2 fusion protein in the presence of Ribi RAS triple adjuvant (monophosphoryl lipid A, trehalose dicorynomycolate, and cell wall skeleton) at initial doses of 25 μg/kg. Animal 6876 was boosted with the unfractionated antigen at 5 μg/kg, while the other two Case-A2 fusion protein-immunized animals (#7014 and #7026) were boosted with the Mab 258 affinity-purified fraction of the Case-A2 fusion protein. A fourth animal (#6874) was immunized with an equivalent amount of the gp70-related carrier sequence. The animals were bled prior to each immunization and at weekly intervals following each immunization. All three Case-A2 fusion protein-immunized animals generated significant antibody titers against the fusion protein immediately after the first boost. These titers decayed after several months, and a potent anamnestic response was observed in all animals following the second boost.

Both macaques immunized with the purified Case-A2 fusion protein produced antibodies that reacted with heterologous gp120s as well as the V1/V2 domains derived from Env sequences of a number of unrelated HIV-1 isolates, including one Thai clade E sequence (FIGS. 7A–C). These antibodies appear to recognize common is conserved sequences, as evidenced by the fact that almost all of the reactivity of antibodies induced by the Case-A2 fusion protein for two unrelated recombinant Env proteins (derived from the Ba-L and 451 isolates) was absorbed by the heterologous SF162 V1/V2 protein (FIGS. 8A and 8B). In initial assays, we found that sera of the three animals immunized with the Case-A2 fusion protein, but not that of the control animal, were able to neutralize the macrophage-tropic NL-HX-ADA virus. These results indicated that the Case-A2 fusion protein was able to induce crossreactive antibodies against native gp120 epitopes that possessed neutralizing activity for at least one macrophage-tropic isolate.

To further characterize the antibodies elicited by Case-A2 fusion protein, the V1/V2-specific IgG fraction of the immune sera was isolated by sequential immunoaffinity chromatography on a column containing the immobilized gp70-related carrier protein, followed by passage over a column containing the complete V1/V2 fusion protein. This resulted in removal of more than 95% of all V1/V2 domain reactive antibodies. A portion of the V1/V2 domain reactive antibodies bound to the second column was recovered by sequential elution with low pH buffers followed by elution with buffer containing 8M guanidine hydrochloride. After extensive buffer exchange, the isolated antibodies were quantitated and tested for HIV-1 neutralizing activities.

All of the eluted antibody fractions possessed neutralizing activities for a number of macrophage-tropic isolates, with the lower pH and GuHCl antibody fraction generally being more potent than that eluted at pH 2.4 (FIGS. 9A–9C and 10A–10C). In addition to NL-HX-ADA, viruses neutralized included Ba-L, a virus recombinant derived from NL-HX-ADA that contained the Case-A2 V1/V2 domain, and a clade C primary isolate from Malawi, 92W959C.

Figure 11A:
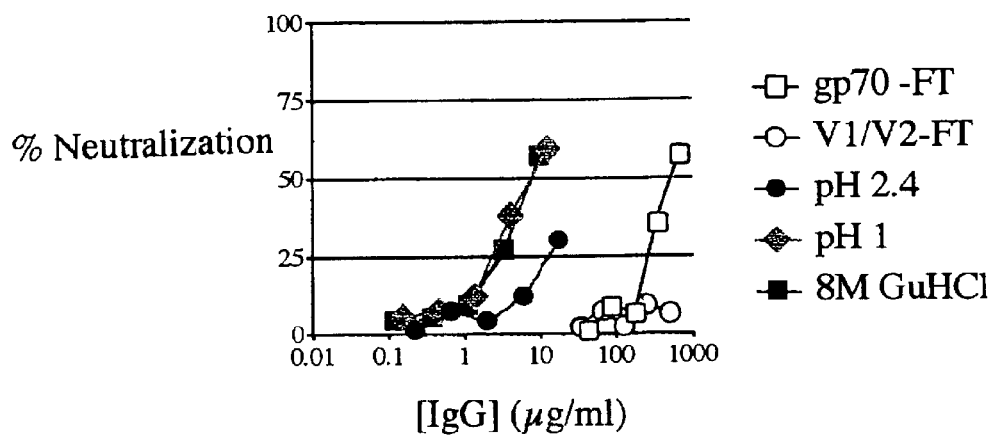
FIGS. 11A–11B: Neutralization of HIV-1 primary isolate 92US716B by fractionated macaque 6876 serum (FIG. 11A) and fractionated macaque 7026 serum. Fractions tested included: gp70 flow through (closed squares), V1/V2 flow through (closed circles), pH 2.4 wash (closed circles), pH 1 wash (closed diamonds), and 8M GuHCl wash (closed squares). Whole serum (closed circles) was also tested.
Figure 11B:
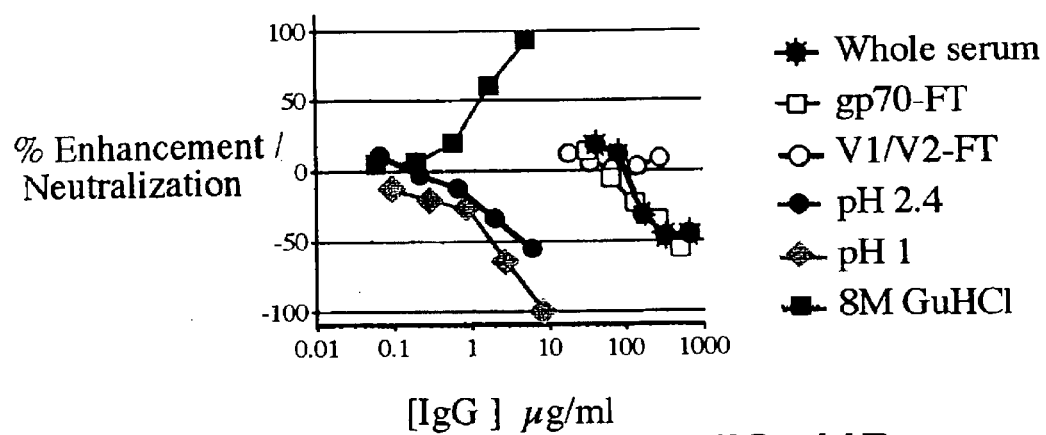
Figure 13:
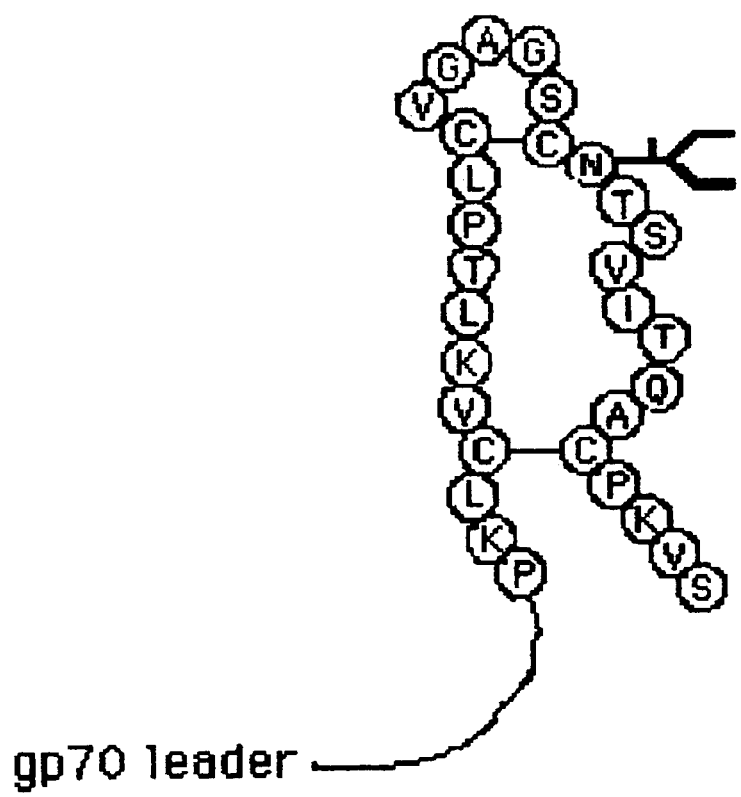
FIG. 13: V1/V2 stem analog having a GAG inserted between the ends of the C1 and C2 regions.

A different result was obtained for one primary isolate, 92US716B (FIGS. 11A and 11B). Whereas the 6876 serum and V1/V2 domain reactive antibodies isolated from this serum also neutralized this virus, the 7026 serum enhanced infectivity. This enhancing activity was removed upon absorption of the V1/V2 domain specific antibodies, and was recovered in the low pH eluates of this column, demonstrating that it was antigen-specific. Interestingly, the antibodies eluted in the GuHCl fraction of this column possessed neutralizing activity for the 92US716 isolate. This indicated that this serum possessed both neutralizing and enhancing antibodies for the 92US716B virus, and that the enhancing activity dominated in the unfractionated serum.

An unexpected result was that, in contrast to the efficient neutralization of NL-HX-ADA and NL-Case-A2-ADA, antibodies in the GuHCl fraction did not neutralize two related molecular recombinants that contained the identical V1/V2 domain, but with T cell-tropic V3–V5 regions (FIGS. 12A–12D). This result suggests that the neutralizing activity of these antibodies was specific for macrophage-tropic isolates. This supports a model in which the key V1/V2 epitopes that are targeted by these antibodies function specifically in CCR5-dependent infections, either by virtue of a direct interaction with a site on gp120 that interacts with the CCR5 receptor, or as a result of inducing a conformational change in gp120 that is specific for macrophage-tropic envelope proteins.

Preparation of Monoclonal Antibodies

Monoclonal antibodies, which are homogeneous populations of antibodies to a particular antigen, can be prepared using the V1/V2 fusion proteins described above and standard hybridoma technology (see, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. Monoclonal antibodies of human origin can be derived either by directly transforming human B cells, or by standard hybridoma techniques, using strains of mice that hve been engineered to produce only human immunoglobulins (Fishwild et al., Nat. Biotech. 14:845, 1996; Mendez et al., Nat. Genet. 15:146, 1997; Abgenix, Inc., Freemont, Calif.; GenPharm, Inc., Palo Alto, Calif.). The hybridoma producing the mAb of this invention may be cultivated in vitro or in vivo. The ability to produce high titers of mAbs in vivo makes this the presently preferred method of production.

Once produced, polyclonal or monoclonal antibodies are tested for specific gp120 recognition by Western blot or immunoprecipitation analysis by standard methods, e.g., as described in Ausubel et al., supra. Among the antibodies that bind to V1/V2 fusion proteins are C936, K19B3, SC258, and 684-238.

Nucleic Acid Molecules Encoding a Protein of the Invention

The invention includes nucleic acid molecules encoding the proteins of the invention. The nucleic acid sequences can be naturally occurring sequences (e.g., sequences clone from HIV-1 itself) or sequences that differ from those that occur naturally, but, due to the degeneracy of the genetic code, encode the same polypeptide. In addition, these nucleic acid molecules are not limited to sequences that only encode, and thus, can include coding sequence that encodes a carrier polypeptide, as well as some or all of the non-coding sequences, e.g., regulatory sequences.

The nucleic acid molecules of the invention can be synthesized (for example, by phosphoramidite-based synthesis) or obtained from a natural source (e.g., a virus or a recombinant virus).

The isolated nucleic acid molecules of the invention encompass fragments that are not found as such in the natural state. Thus, the invention encompasses recombinant molecules, such as those in which a nucleic acid sequence is incorporated into a vector (for example, a plasmid or viral vector) or is joined to a second nucleic acid sequence sich that the joined sequences encode a chimeric protein.

The invention also features a vector that includes a nucleic acid molecule encoding a protein of the invention. In various specific embodiments, the vector is an expression vector, and can include a regulatory element such as the cytomegalovirus hCMV immediate early gene, the early promoter of SV40 adenovirus, the late promoter of SV40 adenovirus, the lac system, the tr=system, the TAC system, the TRC system, the major operator and promoter regions of phage, the control regions of fd coat protein, the promoter for 3-phosphoglycerate kinase, the promoters of acid phosphatase, and the promoters of the yeast mating factors. The vector can be a plasmid or a virus, such as a retrovirus.

Particularly preferred are expression vectors which express the protein of the invention as part of a fusion protein with gp70. Suitable fusion protein expression vectors are described in U.S. Pat. No. 5,643,756 (Kayman et al.), hereby incorporated by reference.

In another aspect, the invention features a genetically engineered host cell, particularly a eukaryotic cell, which includes a vector, as described above.

Use

The proteins of the invention can be combined with a suitable adjuvant (e.g., an aluminum salt) to create a vaccine. Vaccine formulations will contain an effective amount of the selected protein antigen (i.e., an amount of protein which, when combined with adjuvant, will cause the subject (e.g., chimpanzees, maques, baboons, or humans) vaccinated to produce sufficient specific immunological response to provide for protection against subsequent exposure to HIV. The vaccine compositions may also be used therapeutically treatment of subjects (e.g., chimpanzees, maques, baboons, or humans) already infected with HIV.

In many cases the vaccine will need to be administered more than once to bring about the desire therapeutic or prophylactic effect. The precise protocol (dosage and frequency of administration can be established through standard clinical trials. Those skilled in the art will be able to design suitable clinical-trials using the results of animal trials (e.g., studies conducted in non-human primates). Dosages may range from 0.1 mg/dose to 1 mg/dose, 10 mg/dose, 100 mg/dose, or 250 mg/dose. The effective amount of a given protein will depend on a number of factors including antigenicity and purity.

The antigen and adjuvant are generally suspended in a small volume (generally 2 ml or less) of a pharmaceutically acceptable carrier.

Adjuvants and vaccination protocols are discussed in U.S. Pat. No. 5,614,612, hereby incorporated by reference.

REFERENCES

Ashkenazi, A., Smith, D. H., Marsters, S. A., Riddle, L., Gregory, T. J., Ho, D. D., and Capon, D. J. (1991). Resistance of primary HIV-1 isolates to soluble CD4 is independent of CD4-gp120 binding affinity. Proc. Natl. Acad. Sci. USA 88, 7056–7060.

Bebbington, C. R., Renner, G., Thomson, S., King, D., Abrams, D., and Yarrangton, G. T. (1992). High-level expression of a recombinant antibody from myeloma cells using a glutamine synthetase gene as an amplifiable selectable marker. Biotechnology 10, 169–175.

Bou-Habib, D. C., Roderiquez, G., Oravecz, T., Berman, P. W., Lusso, P., and Norcross, M. A. (1994). Cryptic nature of envelope V3 region epitopes protects primary monocytropic human immunodeficiency virus type 1 from antibody neutralization. J. Virol. 68, 6006–6013.

Burton, D. R., Pyati, J., Koduri, R., Sharp, S. J., Thornton, G. B., Parren, P. W. H. I., Sawyer, L. S. W., Hendry, R. M., Dunlop, N., Nara, P. L., Lamacchia, M., Garraty, E., Stiehm, E. R., Bryson, Y. J., Cao, Y., Moore, J. P. Ho, D. D., and III, C. F. B. (1994). Efficient neutralization of primary isolates of HIV-1 by a recombinant human monoclonal antibody. Science 266, 1024–1027.

Chamat, S., Nara, P., Berquist, L., Whalley, A., Morrow, W. J. W., Kohler, H., and Kang, C.-Y. (1992). Two major groups of neutralizing anti-gp120 antibodies exist in HIV-infected individuals. J. Immunol. 149, 649–654.

Conley, A. J., Gorny, M. K., II, J. A. K., Boots, L. J., Ossorio-Castro, M., Koenig, S., Lineberger, D. W., Emini, E. A., Williams, C., and Zolla-Pazner, S. (1994). Neutralization of primary human immunodeficiency virus type 1 isolates by the broadly reactive anti-V3 monoclonal antibody, 447–52D. J. Virol. 68, 6994–7000.

Conley, A. J., II, J. A. K., Boots, L. J., Tung, J.-S., Arnold, B. A., Keller, P. M., Shaw, A. R., and Emini, E. A. (1994). Neutralization of divergent human immunodeficiency virus type 1 variants and primary isolates by IAM-41-2F5, an anti-gp41 human monoclonal antibody. Proc. Natl. Acad. Sci. USA 91, 3348–3352.

Cordell, J., Moore, J. P., Dean, C. J., Klasse, P. J., Weiss, R. A., and McKeating, J. A. (1991). Rat monoclonal antibodies to nonoverlapping epitopes of Human Immunodeficiency Virus Type 1 gp120 block CD4 binding in vitro. Virology 185, 72–79.

D'Souza, M. P., Geyer, S. J., Hanson, C. V., Hendry, R. M., Milman, G., and Investigators, C. (1994). Evaluation of monoclonal antibodies to HIV-1 by neutralization and binding assays: an international collaboration. AIDS 8, 169–181.

D'Souza, M. P., Milman, G., Bradac, J. A., McPhee, D., Hanson, C. V., Hendry, R. M., and Investigators, C. (1995). Neutralization of primary HIV-1 isolates by anti-envelope monoclonal antibodies. AIDS 9, 867–874.

Fouts, T. R., Binley, J. M., A, A. T., Robinson, J. E., and Moore, J. P. (1997). Neutralization of the human immunodeficiency virus type 1 primary isolate JR-FL by human monoclonal antibodies correlates with antibody binding to the oligomeric form of the envelope glycoprotein complex. J. Virol. 71, 2779–2785.

Fishwald, D. M., S. O'Donnel, T. Bengoechea, D. Hudson, F. Harding, S. Bernhard, D. Jones, R. Kay, K. Higgins, S. Schramm, and N. Lonberg, 1996. High-avidity human IgG kappa monoclonal antibodies from a novel strain of minilocus transgenic mice. Nat. Biotechnol. 14:845–851.

Fung, M. S. C., Sun, C. R. Y., Gordon, W. L., Liou, R. S., Chang, T. W., Sun, W. N. C., Daar, E. S., and Ho, D. D. (1992). Identification and characterization of a neutralization site within the second variable region of human immunodeficiency virus type 1 gp120. J. Virol. 66, 848–856.

Gao, F., Yue, L., Stevenson, C., Thornton, C. L., Robertson, D. L., McCutchan, F. E., Bradac, J. A., Sharp, P. M., Hahn, B. H., and Characterization, W. N. f. H. I. a. (1994). Genetic variation of HIV type 1 in four World Health Organization-sponsored vaccine evaluation sites: generation of functional envelope (glycoprotein 160) clones representative of sequence subtypes A, B, C and E. AIDS Res. Hum. Retroviruses 10, 1357–1366.

Golding, H., D'Souza, M. P., Bradac, J., Mathieson, B., and Fast, P. (1994). Neutralization of HIV-1: Meeting report. AIDS Res. Hum. Retroviruses 10, 633–643.

Gomatos, P. J., Stamatos, N. M., Gendelman, H. E., Fowler, A., Hoover, D. L., Kalter, D. C., Burke, D. S., Tramont, E. C., and Meltzer, M. S. (1990). Relative inefficiency of soluble recombinant CD4 for inhibition of infection by monocyte-tropic HIV in monocytes and T cells. J. Immunol. 144, 4183–4188.

Gorny, M. K., Xu, J.-Y., Karwowska, S., Buchbinder, A., and Zolla-Pazner, S. (1993). Repertoire of neutralizing human monoclonal antibodies specific for the V3 domain of HIV-1 gp120. J. Immunol. 150, 635–643.

Guo, M. M. L., and Hildreth, J. E. K. (1995). HIV acquires functional adhesion receptors from host cells. AIDS Res. Hum. Retroviruses 11, 1007–1013.

Hanson, C. V. (1994). Measuring vaccine-induced HIV neutralization: Report of a Workshop. AIDS Res. Hum. Retroviruses 10, 645–648.

Hildreth, J. E. K., and Orentas, R. J. (1989). Involvement of a leukocyte adhesion receptor (LFA-1) in HIV-induced syncytium formation. Science 244, 1075.

Ho, D. D., Fung, M. S. C., Cao, Y., Li, X. L., Sun, C., Chang, T.-W., and Sun, N. C. (1991). Another discontinuous epitope on glycoprotein gp120 that is important in human immunodeficiency virus type 1-neutralization is identified by a monoclonal antibody. Proc. Natl. Acad. Sci. USA 88, 8949–8952.

Ho, D. D., McKeating, J. A., Li, X. L., Moudgil, T., Daar, E. S., Sun, N.-C., and Robinson, J. E. (1991). Conformational epitope on gp120 important in CD4 binding and human immunodeficiency virus type 1 neutralization identified by a human monoclonal antibody. J. Virol. 65, 489–493.

Honnen, W. J., Wu, Z., Kayman, S. C., and Pinter, A. (1996). Potent neutralization of a macrophage-tropic HIV-1 isolate by antibodies against the V1/V2 domain of gp120. In Vaccines 1996: Molecular Approaches to the Control of Infectious Diseases, E. N. F. Brown, D. Burton and J. Mekalanos, eds.: Cold Spring Harbor Laboratory Press), pp. 289–297.

Kayman, S. C., Wu, Z., Revesz, K., Chen, H.-C., Kopelman, R., and Pinter, A. (1994). Presentation of native epitopes in the V1/V2 and V3 domains of HIV-1 gp120 by is fusion glycoproteins containing fragments of gp120. J. Virol. 68, 400–410.

Lee, S., Peden, K., Dimitrov, D. S., Broder, C. C., Manishewitz, J., Denisova, G., Gershoni, J. M., and Golding, H. (1997). Enhancement of human immunodeficiency virus type 1 envelope-mediated fusion by a CD4-gp120 complex-specific monoclonal antibody. J. Virol. 71, 6037–6043.

Mascola, J., Weislow, O., Snyder, S., Belay, S., Yeager, M., McCutchan, F., McNeil, J., Burke, D., and Walker, M. C.

(1994). Neutralizing antibody activity in sera from human immunodeficiency virus type 1 vaccine recipients from the AIDS Vaccine Clinical Trials Network. AIDS Res. Hum. Retroviruses 10:(Suppl 2), S55.

Matthews, T. J. (1994). Dilemma of neutralization resistance of HIV-1 field isolates and vaccine development. AIDS Res. Hum. Retroviruses 10, 631–632.

McKeating, J. A., Shotton, C., Cordell, J., Graham, S., Balfe, P., Sullivan, N., Charles, M., Page, M., Blomstedt, A., Olofsson, S., Kayman, S. C., Wu, Z., Pinter, A., Dean, C., Sodroski, J., and Weiss, R. A. (1993). Characterization of neutralizing monoclonal antibodies to linear and conformation-dependent epitopes within the first and second variable domains of human immunodeficiency virus type 1 gp120. J. Virol. 67, 4932–4944.

Mendez, M., L. Green, J. Corvalan, X. Jia, C. Maynard-Currie, X. Yang, M. Gallo, D. Louis, D. Lee, K. Erickson, J. Luna, C. Roy, H. Abderrahim, F. Kirschenbaum, M. Noguchi, D. Smith, A. Fukushima, J. Hales, S. Klapholz, M. Finer, et al. 1997. Functional transplant of megabase human immunoglobulin loci recapitulates human antibody response in mice. Nat. Genet., 15:146–156.

Moore, J., Cao, Y., Qing, L., Sattentau, Q. J., Pyati, J., Koduri, R., Robinson, J., III, C. F. B., Burton, D. R., and Ho, D. D. (1995). Primary isolates of human 0.20 immunodeficiency virus type 1 are relatively resistant to neutralization by monoclonal antibodies to gp120, and their neutralization is not predicted by studies with monomeric gp120. J. Virol. 69, 101–109.

Moore, J. P., and Ho, D. D. (1993). Antibodies to discontinuous or conformationally sensitive epitopes on the gp120 glycoprotein of Human Immunodeficiency Virus type 1 are highly prevalent in sera of infected humans. J. Virol. 67, 863–975.

Moore, J. P., Sattentau, Q. J., Yoshiyama, H., Thali, M., Charles, M., Sullivan, N., Poon, S.-W., Fung, M. S., Traincard, F., Pincus, M., Robey, G., Robinson, J. E., Ho, D. D., and Sodroski, J. (1993). Probing the structure of the V2 domain of human immunodeficiency virus type 1 surface glycoprotein gp120 with a panel of eight monoclonal antibodies: human immune response to the V1 and V2 domains. J. Virol. 67, 6136–6151.

Muster, T., Guinea, R., Trkola, A., Purtscher, M., Klima, A., Steindl, F., Palese, P., and Kattinger, H. (1994). Cross-neutralizing activity against divergent human immunodeficiency virus type 1 isolates induced by the gp41 sequence ELDKWAS. J. Virol. 68, 4031–4034.

Myers, G., Foley, B., Mellors, J. W., Korber, B., Leang, K.-T., Wain-Hobson, S., eds., (1996) Human Retroviruses and AIDS 1996. Los Alamos National Laboratory, Los Alamos, N. Mex.

Olshevsky, U., Helseth, E., Furman, C., Li, J., Haseltine, W., and Sodroski, J. (1990). Identification of individual human immunodeficiency virus type 1 gp120 amino acids important for CD4 receptor binding. J. Virol. 64, 5701–5707.

Pincus, S. H., Messer, K. G., Nara, P. L., Blattner, W. A., Colclough, G., and Reitz, M. (1994). Temporal analysis of the antibody response to HIV envelope protein in HIV-infected laboratory workers. J. Clin. Invest. 93, 2505–2513.

Sawyer, L. S. W., Wrin, M. T., Crawford-Miksza, L., Potts, B., Wu, Y., Weber, P. A., Alfonso, R. D., and Hanson, C. V. (1994). Neutralization sensitivity of human immunodeficiency virus type 1 is determined in part by the cell in which the virus is propagated. J. Virol. 68, 1342–1349.

Schutten, M., Andeweg, A. C., Bosch, M. L., and Osterhaus, A. D. M. E. (1995). Enhancement of infectivity of a non-syncytium inducing HIV-1 by sCD4 and by human antibodies that neutralize syncytium inducing HIV-1. Scand. J. Immunol. 41, 18–22.

Stamatatos, L., Zolla-Pazner, S., Gorny, M. K., and Cheng-Mayer, C. (1997). Binding of antibodies to virion-associated gp120 molecules of primary-like human immunodeficiency virus type 1 (HIV-1) isolates: effect on HIV-1 infection of macrophages and peripheral blood mononuclear cells. Virology 229, 360–369.

Thali, M., Furman, C., Ho, D. D., Robinson, J., Tilley, S., Pinter, A., and Sodroski, J. (1992). Discontinuous, conserved neutralization epitopes overlapping the CD4 binding region of the HIV-1 gp120 envelope glycoprotein. J. Virol. 66, 5635–5641.

Tilley, S. A., Honnen, W. J., Racho, M. E., Hilgartner, M., and Pinter, A. (1991). Human monoclonal antibodies against the putative CD4 binding site and the V3 loop of HIV gp120 act in concert to neutralize virus. VII Intl. Conf. on AIDS abstr. 70, Florence, Italy. Tilley, S. A., and Pinter, A. (1993). Human and chimpanzee monoclonal antibodies (MAbs) with anti-viral activity against HIV-1. AIDS Res. Reviews 3, 255–287.

Trkola, A., Pomales, A. B., Yuan, H., Korber, B., Maddon, P. J., Allaway, G. P., Katinger, H., III, C. F. B., Burton, D. R., Ho, D. D., and Moore, J. P. (1995). Cross-clade neutralization of primary isolates of human immunodeficiency virus type 1 by human monoclonal antibodies and tetrameric CD4-IgG. J. Virol. 69, 6609–6617.

Trkola, A., Purtscher, M., Muster, T., Ballaun, C., Buchacher, A., Sullivan, N., Srinivasan, K., Sodroski, J., Moore, J. P., and Katinger, H. (1996). Human monoclonal antibody 2G12 defines a distinctive neutralization epitope on the gp120 glycoprotein of human immunodeficiency virus type 1. J. Virol. 70, 1100–1108.

VanCott, T., Bethke, F. R., Burke, D. S., Redfield, R. R., and Birx, D. L. (1995). Lack of induction of antibodies specific for conserved, discontinuous epitopes of HIV-1 envelope glycoproteins by candidate AIDS vaccines. J. Immunol. 155, 4100–4110.

VanCott, T. C., Polonis, V. R., Loomis, L. D., Michael, N. L., Nara, P. L., and Birx, D. L. (1995). Differential role of V3-specific antibodies in neutralization assays is involving primary and laboratory-adapted isolates of HIV type 1. AIDS Res. Hum. Retroviruses 11, 1379–1391.

Vijh-Warrier, S., Pinter, A., Honnen, W. J., and Tilley, S. A. (1996). Synergistic neutralization of HIV-1 by a chimpanzee monoclonal antibody against the V2 domain of gp120 in combination with monoclonal antibodies against the V3 loop and the CD4-binding site. J. Virol. 70, 4466–4473.

Wang, N., Zhu, T., and Ho, D. D. (1995). Sequence diversity of V1 and V2 domains of gp120 from human immunodeficiency virus type 1: lack of correlation with viral phenotype. J. Virol. 69, 2708–2715.

Warrier, S., Pinter, A., Honnen, W. J., Girard, M., Muchmore, E., and Tilley, S. A. (1994). A novel glycan-dependent epitope in the V2 domain of human immunodeficiency virus type 1 gp120 is recognized by a highly potent neutralizing chimpanzee monoclonal antibody. J. Virology 68, 4636–4642.

Westervelt, P., Trowbridge, D. B., Epstein, L. G., Blumberg, B. M., Li, Y., Hahn, B. H., Shaw, G. M., Price, R. W., and Ratner, L. (1992). Macrophage tropism determinants of human immunodeficiency virus type I in vivo. J. Virol. 66, 2577–2582.

Wu, Z., Kayman, S. C., Revesz, K., Chen, H. C., Warrier, S., Tilley, S. A., McKeating, J., Shotton, C., and Pinter, A.

(1995). Characterization of neutralization epitopes in the V2 region of HIV-1 gp120: role of conserved glycosylation sites in the correct folding of the V1/V2 domain. J. Virol. 69, 2271–2278.

What is claimed is:

1. A protein comprising a gp120 V1/V2 domain of an HIV-1 strain and not comprising the gp120 V3 domain of an HIV-1 strain, wherein said protein does not substantially bind CD4, said gp120 V1/V2 domain of said protein displaying an epitope which is recognized by an antibody which neutralizes at least one HIV-1 primary isolate with a $ND_{90}$ of less than 100 µg/ml.

2. The protein of claim 1, wherein said V1/V2 domain epitope is recognized by an antibody which neutralizes at least one HIV-1 primary isolate from each of at least two different clades with a $ND_{90}$ of less than 100 µg/ml.

3. The protein of claim 1, wherein said two different clades are selected from the group consisting of clade A, clade B, clade C, clade D, and clade E.

4. The protein of claim 1, wherein said V1/V2 domain epitope is recognized by an antibody which neutralizes at least two HIV-1 primary isolates of the same clade with a $ND_{90}$ of less than 100 µg/ml.

5. The protein of claim 3, wherein said V1/V2 domain epitope is recognized by an antibody which neutralizes at least one HIV-1 primary isolate of at least three different clades selected from the group consisting of clade A, clade B, clade C, clade D, and clade E, with a $ND_{90}$ of less than 100 µg/ml.

6. The protein of claim 1 wherein said $ND_{90}$ is less than 50 µg/ml.

7. The protein of claim 1 wherein said $ND_{90}$ is less than 20 µg/ml.

8. The protein of claim 1 wherein said $ND_{90}$ is less than 10 µg/ml.

9. The protein of claim 1 wherein said $ND_{90}$ is less than 5 µg/ml.

10. The protein of claim 1 wherein said $ND_{90}$ is less than 1 µg/ml.

11. The protein of claim 1 wherein said V1/V2 domain comprises a region that is at least 50% identical to GEIKNCSFNITTSIRDKVQKEYALFYKLDIVPID.

12. The protein of claim 1 wherein said V1/V2 domain comprises a region that is at least 75% identical to GEIKNCSFNITTSIRDKVQKEYALFYKLDIVPID.

13. The protein of claim 1 wherein said V1/V2 domain comprises a region that is at least 90% identical to GEIKNCSFNITTSIRDKVQKEYALFYKLDIVPID.

14. The protein of claim 1 wherein said V1/V2 domain is at least 50% identical to
VKLTPLCVTLNCIDLRNATNATSNSNTT-NTTSSSGGLMMEQGEIKNCSFNITT SIRDKV1KEYALFYKLDJVPIDNPKNSTNYRLISCNT SVITQA (SEQ ID NO:1).

15. The protein of claim 1 wherein said V1/V2 domain is at least 50% identical to
VKLTPLCVTLNCDLRNATNATSNSNTT-NTTSSSGGLMMEQGEIKNCSFNITTSIRDK V1KEYALFYKLDIVPIDNPKNSTNYRLISCNTSVITQA (SEQ ID NO: 1) and not comprising the gp120 V3 domain of an HIV-1 strain, wherein said protein does not substantially bind CD4, said gp120 V1/V2 domain related region displaying an epitope which is recognized by an antibody which neutralizes at least one HIV-1 primary isolate with s ND$_{90}$ of les than 100 μg/ml.

16. The protein of claim 1 wherein said V1/V2 domain is at least 90% identical to
VKLTPLCVTLNCIDLRNATNATSNSNTITN TTSSSGGLMMEQGEIKNCSFNITTSIRDKV1KEYAL FYKLDIVPLDNPKNSTNYRLISCNTSVITQA (SEQ ID NO:1).

17. The protein of claim 1, wherein said protein is a glycoprotein.

18. A protein comprising a gp120 V1/V2 domain of an HIV-1 strain and not comprising a gp120 V3 domain of an HIV-1 strain, wherein said protein does not substantially bind CD4, said protein, when used to immunize a rat, elicits an antibody which neutralizes at least one clade B HIV-1 primary isolate and at least one clade D HIV-1 primary isolate with a ND$_{90}$ of less than 100 μg/ml.

19. Monoclonal antibody which binds the gp120 V1/V2 domain of HIV-1 strain Case-A2 and neutralizes at least one clade B HIV-1 primary isolate and at least one clade D HIV-1 primary isolate with a ND$_{90}$ of less than 100 μg/ml.

20. The monoclonal antibody of claim 19 wherein said antibody neutralizes at least one clade A HIV-1 primary isolate with a ND$_{90}$ of less than 100 μg/ml.

21. A method for stimulating the formation of antibodies that neutralize infection by an HIV viral isolate in at least one mammalian species, which comprises administering to a mammalian subject a composition comprising the protein of claim 1.

22. The method of claim 21 wherein said composition is suspended in a pharmaceutical carrier or vehicle.

23. The method of claim 21 wherein said composition comprises an adjuvant.

24. The method of claim 23 wherein said adjuvant is an aluminum salt.

25. The method of claim 23 wherein said adjuvant is an oil-in-water emulsion comprising a emulsifying agent and a metabolizable oil.

26. The method of claim 21 wherein said composition is administered to said mammalian subject by injection.

27. An nucleic acid molecule encoding the protein of claim 1.

28. An expression vector comprising the nucleic acid molecule of claim 27.

29. A host cell harboring the vector of claim 28.

30. A hybrid protein comprising a first part and a second part, said first part comprising the protein of claim 1, said second part comprising an amino terminal carrier protein comprising all or a portion of Friend MuLV gp70.

31. The protein of claim 30 wherein said portion of gp170 comprises amino acids 1–33 of gp70.

32. A protein comprising a first portion and a second portion, said first portion being a V1/V2 domain region homologous to PCVKLTPCV, said second portion being a V1/V2 domain region homologous to SCNTSVITQACP, said first and second portions being linked by at least one disulfide bond.

* * * * *

SEQUENCE LISTING

<160> NUMBER OF SEQ ID NOS: 30

<210> SEQ ID NO 1
<211> LENGTH: 96
<212> TYPE: PRT
<213> ORGANISM: Human immunodeficiency virus (HIV)

<400> SEQUENCE: 1

```
Val Lys Leu Thr Pro Leu Cys Val Thr Leu Asn Cys Ile Asp Leu Arg
 1               5                  10                  15

Asn Ala Thr Asn Ala Thr Ser Asn Ser Asn Thr Thr Asn Thr Thr Ser
            20                  25                  30

Ser Ser Gly Gly Leu Met Met Glu Gln Gly Glu Ile Lys Asn Cys Ser
        35                  40                  45

Phe Asn Ile Thr Thr Ser Ile Arg Asp Lys Val Gln Lys Glu Tyr Ala
    50                  55                  60

Leu Phe Tyr Lys Leu Asp Ile Val Pro Ile Asp Asn Pro Lys Asn Ser
65                  70                  75                  80

Thr Asn Tyr Arg Leu Ile Ser Cys Asn Thr Ser Val Ile Thr Gln Ala
                85                  90                  95
```

<210> SEQ ID NO 2
<211> LENGTH: 34
<212> TYPE: PRT
<213> ORGANISM: Human immunodeficiency virus (HIV)

<400> SEQUENCE: 2

```
Gly Glu Ile Lys Asn Cys Ser Phe Asn Ile Thr Thr Ser Ile Arg Asp
 1               5                  10                  15

Lys Val Gln Lys Glu Tyr Ala Leu Phe Tyr Lys Leu Asp Ile Val Pro
            20                  25                  30

Ile Asp
```

<210> SEQ ID NO 3
<211> LENGTH: 93
<212> TYPE: PRT
<213> ORGANISM: Human immunodeficiency virus (HIV)

<400> SEQUENCE: 3

```
Leu Lys Pro Cys Val Lys Leu Thr Pro Leu Cys Val Thr Leu His Cys
 1               5                  10                  15

Thr Asn Leu Lys Asn Ala Thr Asn Thr Lys Ser Ser Asn Trp Lys Glu
            20                  25                  30

Met Asp Arg Gly Glu Ile Lys Asn Cys Ser Phe Lys Val Thr Thr Ser
        35                  40                  45

Ile Arg Asn Lys Met Gln Lys Glu Tyr Ala Leu Phe Tyr Lys Leu Asp
    50                  55                  60

Val Val Pro Ile Asp Asn Asp Asn Thr Ser Tyr Lys Leu Ile Asn Cys
65                  70                  75                  80

Asn Thr Ser Val Ile Thr Gln Ala Cys Pro Lys Val Ser
                85                  90
```

<210> SEQ ID NO 4
<211> LENGTH: 7

```
<212> TYPE: PRT
<213> ORGANISM: Human immunodeficiency virus (HIV)

<400> SEQUENCE: 4

Glu Asn Leu Tyr Phe Gln Ser
 1               5

<210> SEQ ID NO 5
<211> LENGTH: 7
<212> TYPE: PRT
<213> ORGANISM: Human immunodeficiency virus (HIV)

<400> SEQUENCE: 5

Glu Asn Leu Tyr Phe Gln Gly
 1               5

<210> SEQ ID NO 6
<211> LENGTH: 28
<212> TYPE: PRT
<213> ORGANISM: Human immunodeficiency virus (HIV)

<400> SEQUENCE: 6

Ser Phe Asn Ile Thr Thr Ser Ile Arg Asp Lys Val Gln Lys Glu Tyr
 1               5                  10                  15

Ala Leu Phe Tyr Lys Leu Asp Val Val Pro Ile Asp
             20                  25

<210> SEQ ID NO 7
<211> LENGTH: 23
<212> TYPE: PRT
<213> ORGANISM: Human immunodeficiency virus (HIV)

<400> SEQUENCE: 7

Tyr Val Ser Asn Arg Gly Asn Arg Met Lys Arg Gln Asn Phe Leu Asn
 1               5                  10                  15

Arg Tyr Ile Ile Ser Val Glu
             20

<210> SEQ ID NO 8
<211> LENGTH: 30
<212> TYPE: PRT
<213> ORGANISM: Human immunodeficiency virus (HIV)

<400> SEQUENCE: 8

Pro Lys Leu Cys Val Lys Leu Thr Pro Leu Cys Val Gly Ala Gly Ser
 1               5                  10                  15

Cys Asn Thr Ser Val Ile Thr Gln Ala Cys Pro Lys Val Ser
             20                  25                  30

<210> SEQ ID NO 9
<211> LENGTH: 15
<212> TYPE: PRT
<213> ORGANISM: Human immunodeficiency virus (HIV)

<400> SEQUENCE: 9

Ala Ser Val Lys Leu Thr Pro Leu Cys Val Thr Leu Asn Ser Ile
 1               5                  10                  15

<210> SEQ ID NO 10
<211> LENGTH: 15
<212> TYPE: PRT
<213> ORGANISM: Human immunodeficiency virus (HIV)

<400> SEQUENCE: 10
```

Val Thr Leu Asn Cys Ile Asp Leu Arg Asn Ala Thr Asn Ala Thr
1               5                   10                  15

<210> SEQ ID NO 11
<211> LENGTH: 15
<212> TYPE: PRT
<213> ORGANISM: Human immunodeficiency virus (HIV)

<400> SEQUENCE: 11

Ala Thr Asn Ala Thr Ser Asn Ser Asn Thr Thr Asn Thr Thr Ser
1               5                   10                  15

<210> SEQ ID NO 12
<211> LENGTH: 15
<212> TYPE: PRT
<213> ORGANISM: Human immunodeficiency virus (HIV)

<400> SEQUENCE: 12

Thr Asn Thr Thr Ser Ser Ser Gly Gly Leu Met Met Glu Gln Gly
1               5                   10                  15

<210> SEQ ID NO 13
<211> LENGTH: 15
<212> TYPE: PRT
<213> ORGANISM: Human immunodeficiency virus (HIV)

<400> SEQUENCE: 13

Met Met Glu Gln Gly Glu Ile Lys Asn Cys Ser Phe Asn Ile Thr
1               5                   10                  15

<210> SEQ ID NO 14
<211> LENGTH: 15
<212> TYPE: PRT
<213> ORGANISM: Human immunodeficiency virus (HIV)

<400> SEQUENCE: 14

Ser Phe Asn Ile Thr Thr Ser Ile Arg Asp Lys Val Gln Lys Glu
1               5                   10                  15

<210> SEQ ID NO 15
<211> LENGTH: 15
<212> TYPE: PRT
<213> ORGANISM: Human immunodeficiency virus (HIV)

<400> SEQUENCE: 15

Ser Ile Arg Asp Lys Val Gln Lys Glu Tyr Ala Leu Phe Tyr Lys
1               5                   10                  15

<210> SEQ ID NO 16
<211> LENGTH: 15
<212> TYPE: PRT
<213> ORGANISM: Human immunodeficiency virus (HIV)

<400> SEQUENCE: 16

Glu Tyr Ala Leu Phe Tyr Lys Leu Asp Ile Val Pro Ile Asp Asn
1               5                   10                  15

<210> SEQ ID NO 17
<211> LENGTH: 19
<212> TYPE: PRT
<213> ORGANISM: Human immunodeficiency virus (HIV)

<400> SEQUENCE: 17

Lys Lys Thr Thr Ser Ile Arg Asp Lys Val Gln Lys Glu Tyr Ala Leu

-continued

```
                1               5                  10                 15

Phe Tyr Lys

<210> SEQ ID NO 18
<211> LENGTH: 14
<212> TYPE: PRT
<213> ORGANISM: Human immunodeficiency virus (HIV)

<400> SEQUENCE: 18

Ser Ile Arg Asp Lys Val Gln Lys Glu Tyr Ala Leu Phe Tyr
  1               5                  10

<210> SEQ ID NO 19
<211> LENGTH: 8
<212> TYPE: PRT
<213> ORGANISM: Human immunodeficiency virus (HIV)

<400> SEQUENCE: 19

Ser Thr Ser Ile Arg Gly Lys Val
  1               5

<210> SEQ ID NO 20
<211> LENGTH: 17
<212> TYPE: PRT
<213> ORGANISM: Human immunodeficiency virus (HIV)

<400> SEQUENCE: 20

Thr Thr Ser Ile Arg Asp Lys Val Gln Lys Glu Tyr Ala Leu Phe Tyr
  1               5                  10                 15

Lys

<210> SEQ ID NO 21
<211> LENGTH: 16
<212> TYPE: PRT
<213> ORGANISM: Human immunodeficiency virus (HIV)

<400> SEQUENCE: 21

Thr Thr Ser Ile Arg Asp Lys Val Gln Lys Glu Tyr Ala Leu Phe Tyr
  1               5                  10                 15

<210> SEQ ID NO 22
<211> LENGTH: 14
<212> TYPE: PRT
<213> ORGANISM: Human immunodeficiency virus (HIV)

<400> SEQUENCE: 22

Thr Thr Ser Ile Arg Asp Lys Val Gln Lys Glu Tyr Ala Leu
  1               5                  10

<210> SEQ ID NO 23
<211> LENGTH: 13
<212> TYPE: PRT
<213> ORGANISM: Human immunodeficiency virus (HIV)

<400> SEQUENCE: 23

Thr Thr Ser Ile Arg Asp Lys Val Gln Lys Glu Tyr Ala
  1               5                  10

<210> SEQ ID NO 24
<211> LENGTH: 12
<212> TYPE: PRT
<213> ORGANISM: Human immunodeficiency virus (HIV)

<400> SEQUENCE: 24
```

```
Thr Thr Ser Ile Arg Asp Lys Val Gln Lys Glu Tyr
 1               5                   10
```

```
<210> SEQ ID NO 25
<211> LENGTH: 15
<212> TYPE: PRT
<213> ORGANISM: Human immunodeficiency virus (HIV)

<400> SEQUENCE: 25

Ser Ile Arg Asp Lys Val Gln Lys Glu Tyr Ala Leu Phe Tyr Lys
 1               5                   10                  15

<210> SEQ ID NO 26
<211> LENGTH: 13
<212> TYPE: PRT
<213> ORGANISM: Human immunodeficiency virus (HIV)

<400> SEQUENCE: 26

Arg Asp Lys Val Gln Lys Glu Tyr Ala Leu Phe Tyr Lys
 1               5                   10

<210> SEQ ID NO 27
<211> LENGTH: 12
<212> TYPE: PRT
<213> ORGANISM: Human immunodeficiency virus (HIV)

<400> SEQUENCE: 27

Asp Lys Val Gln Lys Glu Tyr Ala Leu Phe Tyr Lys
 1               5                   10

<210> SEQ ID NO 28
<211> LENGTH: 365
<212> TYPE: PRT
<213> ORGANISM: Human immunodeficiency virus (HIV)

<400> SEQUENCE: 28

Ala Ala Pro Gly Ser Ser Pro His His His His His Val Tyr Asn
 1               5                   10                  15

Ile Thr Trp Glu Val Thr Asn Gly Asp Arg Glu Thr Val Trp Ala Ile
             20                  25                  30

Ser Gly Asn His Pro Leu Trp Thr Trp Trp Pro Val Leu Thr Pro Asp
         35                  40                  45

Leu Cys Met Leu Ala Leu Ser Gly Pro Pro His Trp Gly Leu Glu Tyr
     50                  55                  60

Gln Ala Pro Tyr Ser Ser Pro Pro Gly Pro Pro Cys Cys Ser Gly Ser
 65                  70                  75                  80

Ser Gly Ser Ser Ala Gly Cys Ser Arg Asp Cys Asp Glu Pro Leu Thr
                 85                  90                  95

Ser Leu Thr Pro Arg Cys Asn Thr Ala Trp Asn Arg Leu Lys Leu Asp
                100                 105                 110

Gln Val Thr His Lys Ser Ser Glu Gly Phe Tyr Val Cys Pro Gly Ser
            115                 120                 125

His Arg Pro Arg Glu Ala Lys Ser Cys Gly Gly Pro Asp Ser Phe Tyr
        130                 135                 140

Cys Ala Ser Trp Gly Cys Glu Thr Thr Gly Arg Val Tyr Trp Lys Pro
145                 150                 155                 160

Ser Ser Ser Trp Asp Tyr Ile Thr Val Asp Asn Asn Leu Thr Thr Ser
                165                 170                 175

Gln Ala Val Gln Val Cys Lys Asp Asn Lys Trp Cys Asn Pro Leu Ala
```

```
                    180                185                190

Ile Gln Phe Thr Asn Ala Gly Lys Gln Val Thr Ser Trp Thr Thr Gly
        195                200                205

His Tyr Trp Gly Leu Arg Leu Tyr Val Ser Gly Arg Asp Pro Gly Leu
        210                215                220

Thr Phe Gly Ile Arg Leu Arg Tyr Gln Asn Leu Gly Pro Arg Val Pro
225                230                235                240

Ile Gly Pro Asn Pro Val Leu Ala Asp Gln Leu Ser Leu Pro Arg Pro
                245                250                255

Asn Pro Leu Pro Lys Pro Ala Lys Ser Pro Pro Ala Ser Val Lys Leu
            260                265                270

Thr Pro Leu Cys Val Thr Leu Asn Cys Ile Asp Leu Arg Asn Ala Thr
            275                280                285

Asn Ala Thr Ser Asn Ser Asn Thr Thr Asn Thr Thr Ser Ser Ser Gly
        290                295                300

Gly Leu Met Met Glu Gln Gly Glu Ile Lys Asn Cys Ser Phe Asn Ile
305                310                315                320

Thr Thr Ser Ile Arg Asp Lys Val Gln Lys Glu Tyr Ala Leu Phe Tyr
                325                330                335

Lys Leu Asp Ile Val Pro Ile Asp Asn Pro Lys Asn Ser Thr Asn Tyr
            340                345                350

Arg Leu Ile Ser Cys Asn Thr Ser Val Ile Thr Gln Ala
            355                360                365

<210> SEQ ID NO 29
<211> LENGTH: 9
<212> TYPE: PRT
<213> ORGANISM: Human immunodeficiency virus (HIV)

<400> SEQUENCE: 29

Pro Cys Val Lys Leu Thr Pro Cys Val
  1               5

<210> SEQ ID NO 30
<211> LENGTH: 12
<212> TYPE: PRT
<213> ORGANISM: Human immunodeficiency virus (HIV)

<400> SEQUENCE: 30

Ser Cys Asn Thr Ser Val Ile Thr Gln Ala Cys Pro
  1               5                  10
```